US012626827B2

(12) United States Patent
Lee

(10) Patent No.:  US 12,626,827 B2
(45) Date of Patent:      May 12, 2026

(54) METHOD, DEVICE, AND SYSTEM FOR PROVIDING META VERSE HEALTHCARE PLATFORM SERVICE FOR NON-FACE-TO-FACE DIAGNOSIS AND SELF-MANAGEMENT

(71) Applicant: MARKHERZ INC., Seongnam-si (KR)

(72) Inventor: Seung Min Lee, Yongin-si (KR)

(73) Assignee: MARKHERZ INC., Seongnam-si (KR)

( * ) Notice: Subject to any disclaimer, the term of this patent is extended or adjusted under 35 U.S.C. 154(b) by 0 days.

(21) Appl. No.: 18/910,002

(22) Filed: Oct. 9, 2024

(65) Prior Publication Data

US 2025/0029737 A1      Jan. 23, 2025

Related U.S. Application Data

(63) Continuation of application No. PCT/KR2023/003446, filed on Mar. 15, 2023.

(30) Foreign Application Priority Data

Apr. 12, 2022    (KR) ........................ 10-2022-0044887

(51) Int. Cl.
*G16H 80/00*        (2018.01)
*G16H 10/60*        (2018.01)
(Continued)

(52) U.S. Cl.
CPC ............. *G16H 80/00* (2018.01); *G16H 10/60* (2018.01); *G16H 40/67* (2018.01); *G16H 50/30* (2018.01)

(58) Field of Classification Search
None
See application file for complete search history.

(56) References Cited

U.S. PATENT DOCUMENTS

2016/0155352 A1*  6/2016  Johnson ................... G09B 5/14
                                                      434/236
2020/0168329 A1*  5/2020  Solie ...................... G16H 10/60
                          (Continued)

FOREIGN PATENT DOCUMENTS

JP          2022-033384 A      3/2022
KR      10-2010-0099881 A      9/2010
                    (Continued)

OTHER PUBLICATIONS

Lee, Sang Min. Ilsan Cha Hospital, Opens First Hospital in Metaverse Platform Geppetto. Medical News). [Retrieved on Jun. 2, 2022]. Retrieved from <URL: http://www.bosa.co.kr/news/articleView. html?idxno=2153042>.

*Primary Examiner* — John P Go
(74) *Attorney, Agent, or Firm* — NKL LAW; Jae Youn Kim

(57) ABSTRACT

According to an embodiment, there is provided a method of providing a metaverse healthcare platform service for non-face-to-face diagnosis and self-management, performed by a device, the method including the steps of: acquiring, when a health state of a first patient is measured through a measuring device for measuring a health state provided in a diagnostic booth, measurement information generated by measuring the health status of the first patient from the measuring device, determining whether non-face-to-face treatment is required for the first patient on the basis of the measurement information, performing control, when it is determined that non-face-to-face treatment for a first treatment subject is required for the first patient, so that a message for guiding to wear an output device is output to a diagnostic booth, performing control, when it is checked that the first patient wears the output device.

3 Claims, 16 Drawing Sheets

(51) Int. Cl.
    *G16H 40/67*          (2018.01)
    *G16H 50/30*          (2018.01)

(56)           References Cited

U.S. PATENT DOCUMENTS

| | | | |
|---|---|---|---|
| 2021/0134444 A1* | 5/2021 | Redlus | G16H 50/30 |
| 2021/0212637 A1* | 7/2021 | Fu | A61B 5/7203 |
| 2022/0076851 A1* | 3/2022 | Kamangar | G06Q 30/0633 |

FOREIGN PATENT DOCUMENTS

| | | |
|---|---|---|
| KR | 10-2012-0003588 A | 1/2012 |
| KR | 10-2017-0115269 A | 10/2017 |
| KR | 10-2285597 B1 | 8/2021 |
| KR | 10-2302207 B1 | 9/2021 |
| KR | 10-2022-0021265 A | 2/2022 |
| KR | 10-2022-0021975 A | 2/2022 |

* cited by examiner

EXTERIOR
(LIGHT AND EASY
TO INSTALL)

INTERIOR
(NEGATIVE PRESSURE
SYSTEM + STERILIZATION)

CHAIR
(METAVERSE SYSTEM)

INSTALLED IN A HOME (EXAMPLE)

GENERAL ENTRANCE

INDEPENDENT SPACE

NON-FACE-TO-FACE METAVERSE TREATMENT BOOTH INSTALLATION AREA 1,800 mm 2,000 mm 1,400 mm

PUBLIC HALLWAY

GENERAL ENTRANCE

NON-FACE-TO-FACE TREATMENT BOOTH ENTRANCE

INSTALLED IN GENERAL INTERNAL MEDICINE (EXAMPLE)

INDEPENDENT SPACE

DOCTOR BUS
PLATFORM

GLOBAL HEALTH
MEDICAL PERSON

PLEASE. SELECT A MEDICAL PERSON

NON-FACE-TO-FACE DOCTOR
BUS TREATMENT BOOTH

GENERAL PUBLIC OR
PATIENT

400

410

420

METHOD, DEVICE, AND SYSTEM FOR PROVIDING META VERSE HEALTHCARE PLATFORM SERVICE FOR NON-FACE-TO-FACE DIAGNOSIS AND SELF-MANAGEMENT

STATEMENT REGARDING FEDERALLY SPONSORED RESEARCH OR DEVELOPMENT

This research was supported by a grant of the Korea Health Technology R&D Project through the Korea Health Industry Development Institute (KHIDI), funded by the Ministry of Health & Welfare, Republic of Korea (grant number: RS-2024-00440088).

TECHNICAL FIELD

The following embodiments relate to a technology for providing a metaverse healthcare platform service for non-face-to-face diagnosis and self-management.

BACKGROUND ART

Recently, as the trend of medical services changes from face-to-face medical care to non-face-to-face medical care, the market for non-face-to-face medical services is expanding, and the need for personal self-diagnosis and emergency treatment is increasing with the increase in blind spots in medical care.

In addition, due to the expansion of the healthcare market, the global digital healthcare market is growing at an annual average of 30%.

Accordingly, a demand for overcoming an infection environment and creating a non-face-to-face medical environment is increasing, there is a demand for the realization of non-face-to-face or minimal face-to-face remote medical services is required, and there is a demand for research on technologies that can create a work and healthcare environment that can minimize the spread of infection.

In addition, a demand for complementing blind spots in healthcare and improving accessibility through self-diagnosis services is increasing, and as learning and experience become widespread due to COVID-19, there is a need to have the ability to respond medically to emergency situations through self-diagnosis and easy management, and there is a demand for research on technologies that can contribute to improving healthcare access for those in self-quarantine, office workers, housewives, and residents of medically vulnerable areas.

In addition, a demand for resolving regional healthcare imbalances and overcoming healthcare inequality, and providing healthcare services that transcend time and space is increasing, and there is a demand for research on technologies that can provide medical infrastructure in environments where medical support is urgent, overcoming the acceleration of the concentration of health care workers in large cities, and creating a service environment accessible to the disabled and elderly with limited mobility.

Meanwhile, a metaverse has recently been spotlighted as a representative service for providing a virtual world to a user. Metaverse is a complex word of meta, which refers to fiction and abstraction, and universe, which refers to the real world, and refers to a three-dimensional virtual world. The core technology of this metaverse is an extended reality (XR) technology, which encompasses a virtual reality (VR), an augmented reality (AR), and a mixed reality (MR).

Therefore, as the demand for non-face-to-face medical services that allow people to feel the same experience as visiting a hospital in a metaverse environment without directly visiting the hospital is increasing, research on a technology related thereto is required.

Prior Art Literature

Patent Document
- (Patent document 1) Korean Registered Patent No. 10-2302207
- (Patent document 2) Korean Laid-Open Patent Application Publication NO. 10-2022-0021975
- (Patent document 3) Korean Laid-Open Patent Application Publication NO. 10-2022-0021265
- (Patent document 4) Korean Laid-Open Patent Application Publication NO. 10-2012-0003588

DISCLOSURE OF THE INVENTION

Technical Problem

According to an embodiment, an object of the present invention is to provide a method, device, and system for providing a metaverse healthcare platform service for non-face-to-face diagnosis and self-management that acquire, when a health state of a first patient is measured through a measuring device for measuring a health state provided in a diagnostic booth, measurement information generated by measuring the health status of the first patient from the measuring device, determine whether non-face-to-face treatment is required for the first patient on the basis of the measurement information, perform control, when it is determined that non-face-to-face treatment for a first treatment subject is required for the first patient, so that a message for guiding to wear an output device is output to a diagnostic booth, perform control, when it is checked that the first patient wears the output device, so that a first list, which is a list of medical persons who are in charge of the first treatment subject, is displayed on the output device, perform control, if the first medical person is selected from the first list through an operating device when the first patient wears the operating device, so that a screen of a first virtual space, in which a treatment room of a first medical person is implemented as a metaverse environment, is displayed on the output device so as to allow the first patient to be connected to the first virtual space, change, when movement within the first virtual space is requested through the operating device, perform control, when movement within the first virtual space is requested through the operating device, so that a point where the first patient is located in the first virtual space is changed and the screen of the first virtual space is displayed with the changed point as a center on the output device, and perform control, when it is checked that the first medical person is connected to the first virtual space, so that the measurement information is displayed on the first virtual space and perform control so that non-face-to-face treatment between the first patient and the first medical person proceeds in the first virtual space.

The object of the present invention is not limited to the object mentioned above, and other objects not mentioned can be clearly understood from the description below.

Technical Solution

According to an embodiment, there is provided a method of providing a metaverse healthcare platform service for non-face-to-face diagnosis and self-management, performed by a device, the method including the steps of: acquiring, when a health state of a first patient is measured through a measuring device for measuring a health state provided in a diagnostic booth, measurement information generated by measuring the health status of the first patient from the measuring device, determining whether non-face-to-face treatment is required for the first patient on the basis of the measurement information, performing control, when it is determined that non-face-to-face treatment for a first treatment subject is required for the first patient, so that a message for guiding to wear an output device is output to a diagnostic booth, performing control, when it is checked that the first patient wears the output device, so that a first list, which is a list of medical persons who are in charge of the first treatment subject, is displayed on the output device, performing control, if the first medical person is selected from the first list through an operating device when the first patient wears the operating device, so that a screen of a first virtual space, in which a treatment room of a first medical person is implemented as a metaverse environment, is displayed on the output device so as to allow the first patient to be connected to the first virtual space, performing control, when movement within the first virtual space is requested through the operating device, so that a point where the first patient is located in the first virtual space is changed, and the screen of the first virtual space is displayed with the changed point as a center change on the output device, and performing control, when it is checked that the first medical person is connected to the first virtual space, so that the measurement information is displayed on the first virtual space and performing control so that non-face-to-face treatment between the first patient and the first medical person proceeds in the first virtual space.

The step of performing control so that the first list is displayed on the output device may include the steps of checking, when treatment details of the first patient is checked through medical information of the first patient, whether there is a medical person who has treated the first patient among medical persons included in the first list, based on the treatment details of the first patient, selecting, when it is checked that there is only one medical person who has treated the first patient in the first list, the medical person who has treated the first patient as a recommended medical person, selecting, when it is checked that there are two or more medical persons who have treated the first patient in the first list, a medical person having the greatest number of treatments among the medical persons who have treated the first patient as a recommended medical person, checking, when it is checked that there is no medical person who has treated the first patient in the first list, whether there is a medical person who is in a treatment waiting state among the medical persons included in in the first list, selecting, when it is checked that there is only one medical person who is in a treatment waiting state in the first list, the medical person who is in the treatment waiting state as a recommended medical person, selecting, when it is checked that there are two or more medical persons who are in a treatment waiting state in the first list, the medical person having the longest waiting among the medical persons who are in the treatment waiting state as a recommended medical person, selecting, when it is checked that there is no medical person who is in a treatment waiting state in the first list, the medical person having the smallest number of reservations among the medical persons included in the first list as a recommended medical person, and performing control, when a recommended medical person is selected from the first list, so that a guide mark for recommending the recommended medical person is displayed on the output device by being overlapped with the first list.

The step of determining whether the non-face-to-face treatment is required for the first patient may include the steps of checking a first numerical value, which is a numerical value obtained by measuring the health state of the first patient through the measuring device, based on the measurement information, checking whether the first numerical value is within a preset normal range, determining, when it is checked that the first numerical value is within the normal range, that the non-face-to-face treatment is not required for the first patient, checking, when it is checked that the first numerical value is out of the normal range, whether the first numerical value is within a preset warning range, determining, when it is checked that the first numerical value is checked is out of the warning range, that re-measurement of the health state of the first patient is required, and determining, when it is checked that the first numerical value is out of the warning range, that non-face-to-face treatment is required for the first patient.

Advantageous Effects

According to an embodiment, since it is possible to provide non-face-to-face medical services that allow people to experience the same experience as visiting a hospital in a metaverse environment by providing a metaverse healthcare platform service for non-face-to-face diagnosis and self-management, there is an effect of capable of creating a non-face-to-face medical environment, complementing blind spots in health care and improving accessibility through self-diagnosis services, and resolving medical imbalances and overcoming healthcare inequalities between regions.

Meanwhile, the effects according to the embodiments are not limited to those mentioned above, and other effects not mentioned can be clearly understood by a person having ordinary skill in the art from the description below.

MODE FOR CARRYING OUT THE INVENTION

Figure 1:
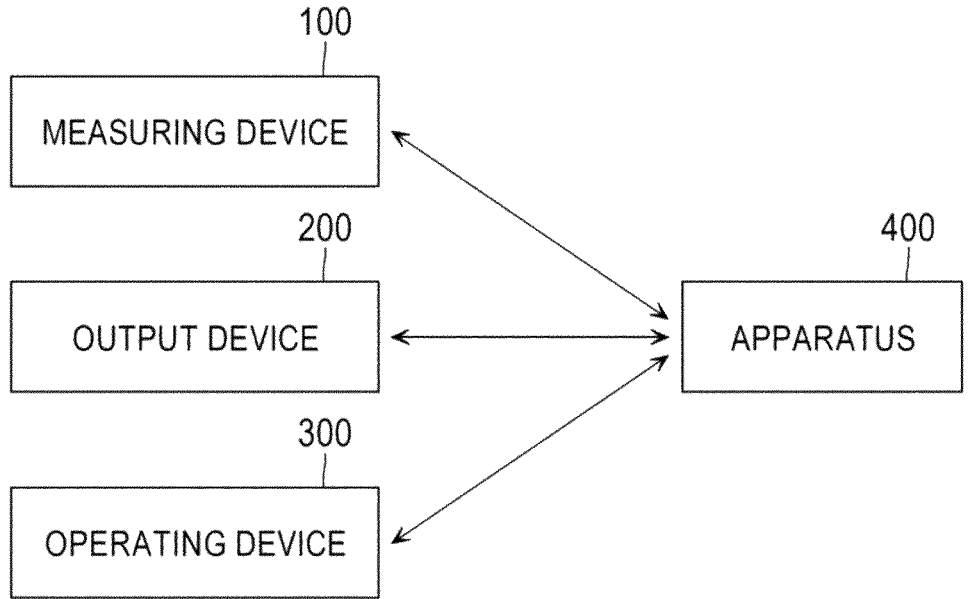
FIG. 1 is a diagram schematically illustrating a configuration of a system according to an embodiment.
Figure 2A:
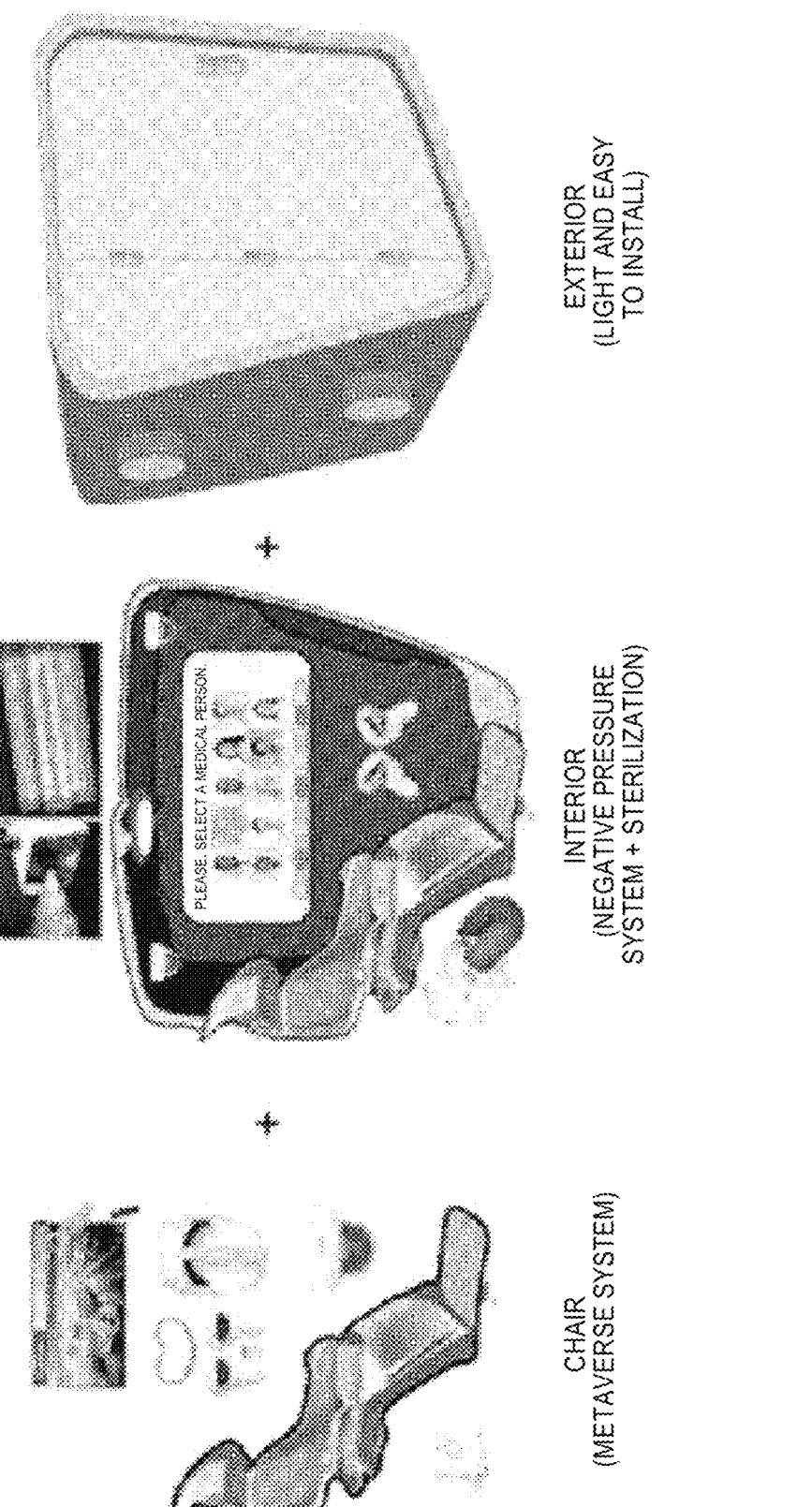
FIGS. 2A-2D are diagrams for describing a diagnostic booth according to an embodiment.
Figure 2B:
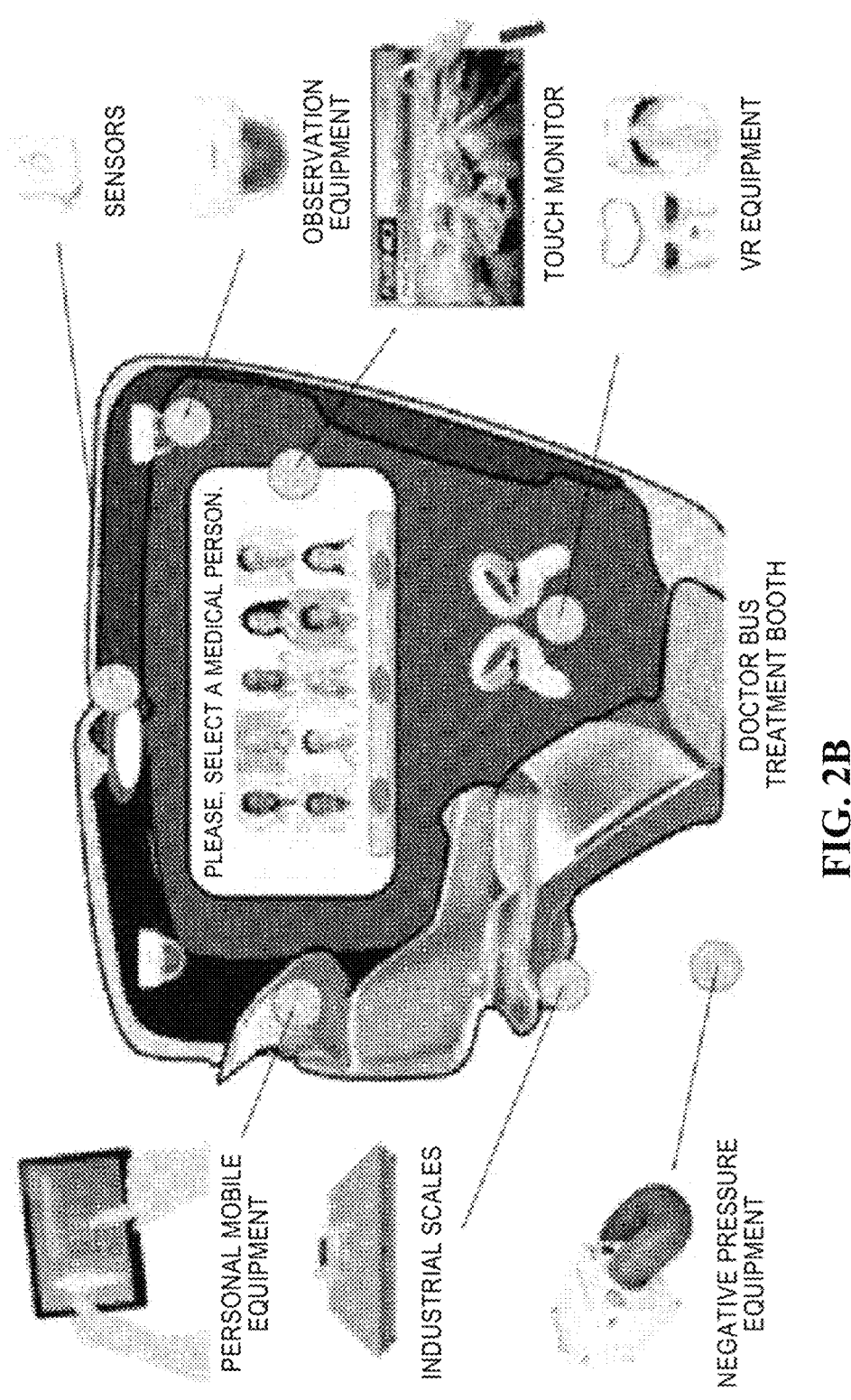
Figure 2C:
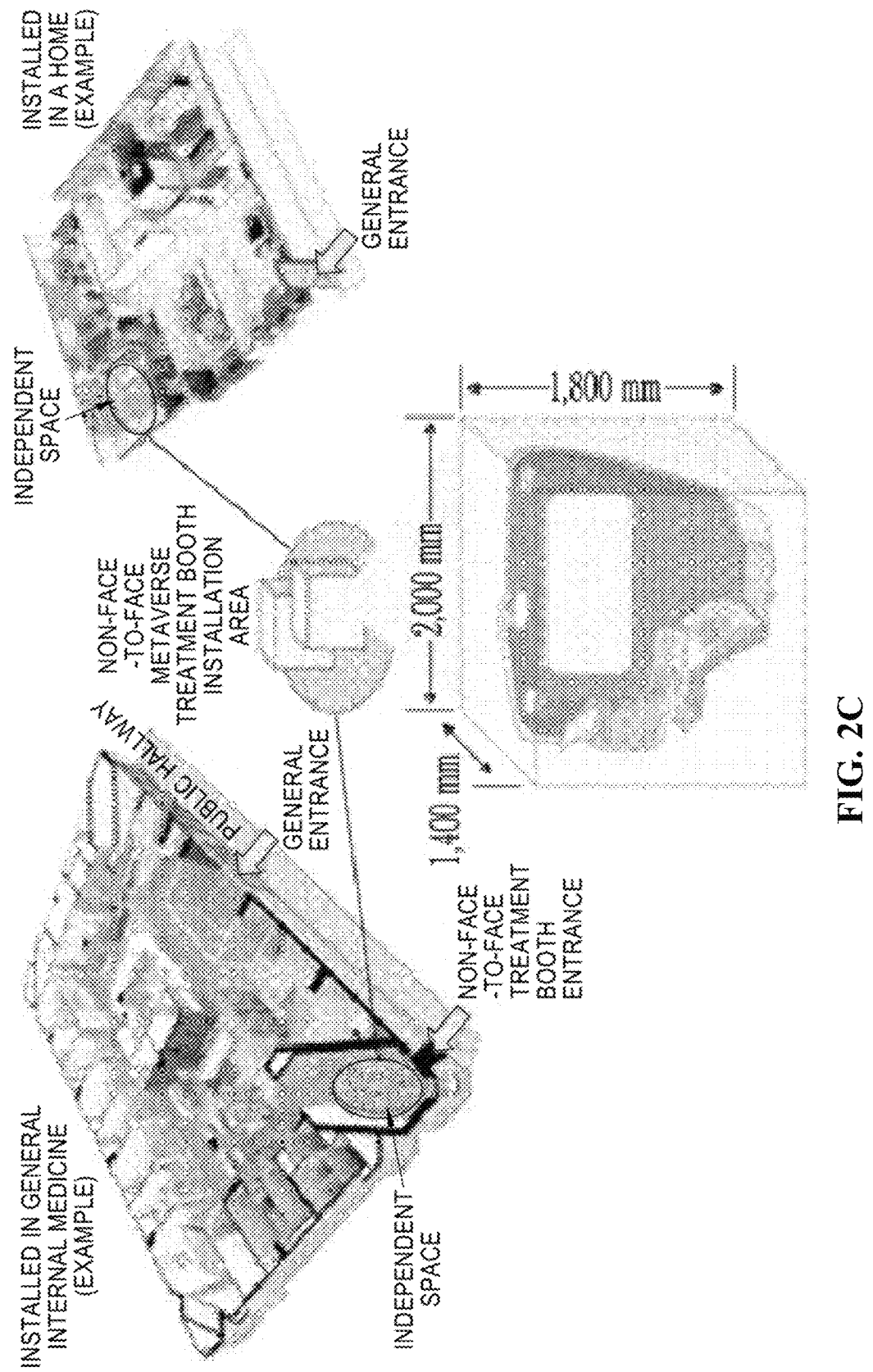
Figure 2D:
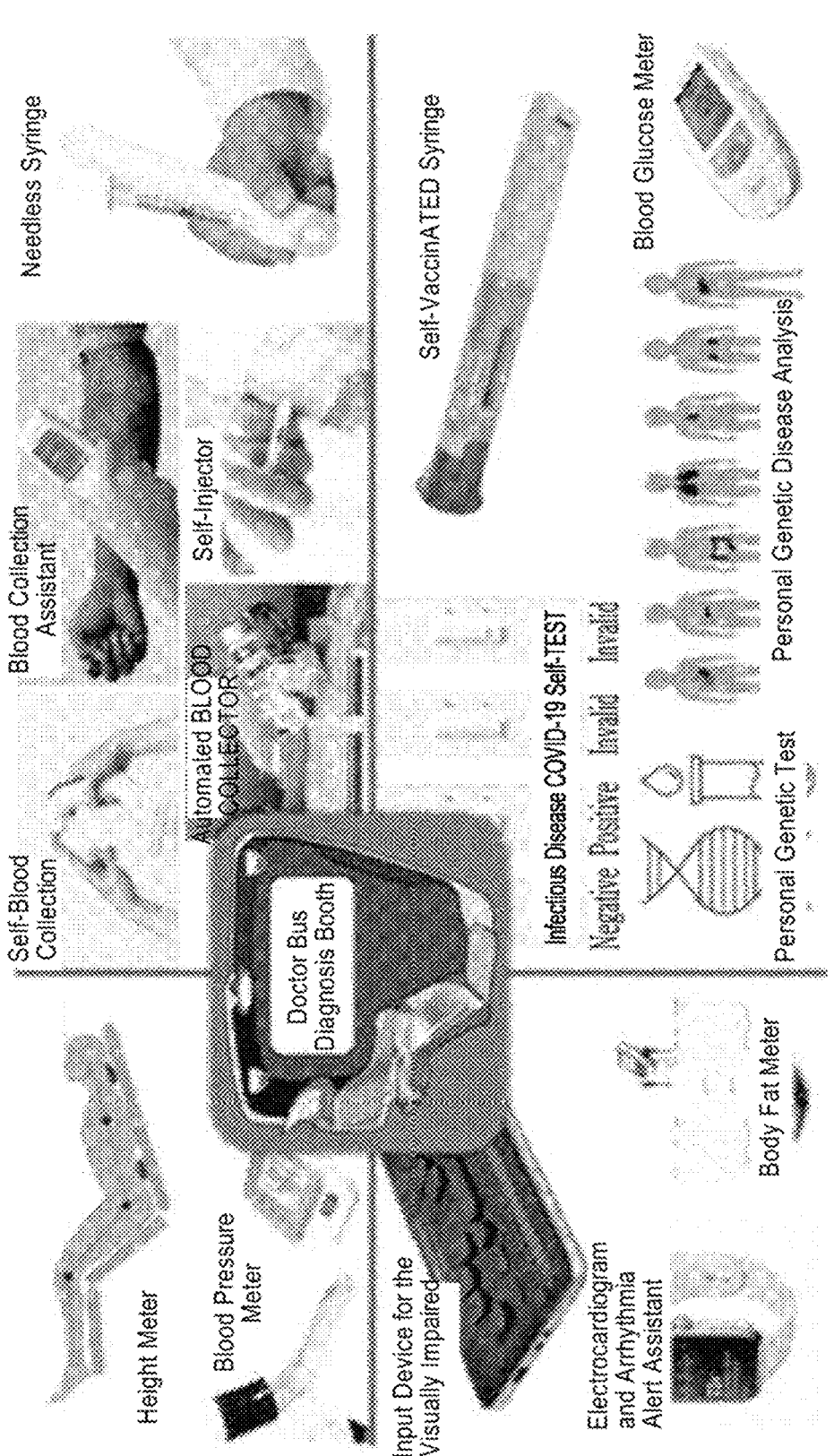

Hereinafter, embodiments are described in detail with reference to the accompanying drawings. However, since various changes may be made to the embodiments, the scope of the patent application is not limited or restricted by these embodiments. It should be understood that all changes, equivalents, or substitutes for the embodiments are included in the scope of the rights.

Specific structural or functional descriptions of the embodiments are disclosed for the purpose of illustration only and may be embodied in various forms. Therefore, the embodiments are not limited to a specific disclosed form, and the scope of the present specification includes changes, equivalents, or substitutes included in the technical idea.

Although the terms "first" or "second" may be used to describe various components, such terms should be interpreted only for the purpose of distinguishing one component from another. For example, a first component may be named a second component, and similarly, a second component may also be named a first component.

When a component is referred to as being "connected" to another component, it should be understood that it may be directly connected or coupled to that other component, but that there may also be other components in between.

The terms used in the embodiment are used for illustrative purposes only and should not be construed as limiting. The singular expression includes the plural expression unless the context clearly indicates otherwise. In this specification, the terms "comprises" or "has" should be understood to indicate the presence of a feature, number, step, operation, component, part, or combination thereof described in the specification, but do not preclude the possibility of the presence or addition of one or more other features, numbers, steps, operations, components, parts, or combinations thereof.

Unless otherwise defined, all terms used herein, including technical or scientific terms, have the same meaning as commonly understood by a person of ordinary skill in the art to which the embodiment belong. Terms that are defined in commonly used dictionaries should be interpreted as having a meaning that is consistent with the meaning they have in the context of the relevant technology, and are not interpreted in an ideal or overly formal sense unless explicitly defined in this application.

In addition, when describing with reference to the accompanying drawings, the same components are given the same reference numerals regardless of the drawing symbols, and redundant descriptions thereof will be omitted. In describing the embodiments, if it is determined that a specific description of a related known technology may unnecessarily obscure the gist of the embodiments, a detailed description thereof will be omitted.

The embodiments can be implemented as various types of products, such as personal computers, laptop computers, tablet computers, smart phones, televisions, smart home appliances, intelligent cars, kiosks, and wearable devices.

FIG. 1 is a diagram schematically illustrating a configuration of a system according to an embodiment.

Referring to FIG. 1, the system according to an embodiment may include a measuring device 100, an output device 200, an operating device 300, and an apparatus 400.

First, the measuring device 100 is a device that measures a health state of a patient and may be electrically connected to the apparatus 400. For example, the measuring device 100 may be provided as a blood pressure measuring device, a blood glucose measuring device, a blood flow measuring device, a heart rate measuring device, an electrocardiogram measuring device, a body fat measuring device, or the like.

That is, the measuring device 100 may be implemented as various types of measuring devices for measuring a health state of a patient for non-face-to-face diagnosis, self-management, and health care. In this case, the measuring device 100 may be implemented as one integrated measuring device, or may be implemented in a state in which a plurality of measuring devices are connected to each other.

The output device 200 is a device that outputs a screen of a virtual space implemented as a metaverse environment, and may be electrically connected to the apparatus 400.

Here, the metaverse is a complex word of meta, which means processing and fiction, and a universe, which means a real world, and refers to a platform where individuals implemented as characters or avatars in a three-dimensional virtual world in the online may communicate with each other and perform real-world activities as they are. Such a metaverse environment may include an extended reality (XR) device that encompasses virtual reality (VR), augmented reality (AR), and mixed reality (MR).

Virtual reality refers to a technology that uses a computer to build a virtual space that does not exist in the real world and then makes the virtual space feel like reality. Augmented reality or mixed reality refers to a technology that adds information generated by a computer to the real world and expresses it, that is, a technology that allows real-time interaction with the user by combining the real world and the virtual world. The metaverse environment in the present invention may be implemented through any one of virtual reality, augmented reality, and mixed reality environments.

The output device 200 is a device that is worn by the patient to output an image of a screen implemented as a metaverse environment, and may be provided as, for example, a head mounted display (HMD), which is a display device that is mounted on the patient's head or eye part and outputs VR/AR images directly in front of the patient's eyes. The head mounted display is a type of wearable image output terminal that supports the patient to experience realistic images, and a display may be mainly mounted on the front of a helmet thereof to output images such as VR/AR images.

The output device 200 may track the gaze of the patient through head movement of the patient wearing the output device 200, and may process an image to be changed and displayed according to the patient's gaze movement through the head tracking. That is, the output device 200 may process the image to be changed in the same direction as the movement of the patient's head by digitizing a rotation angle and speed of the patient's head. For example, when the head of the patient rotates to the right, the image on the screen may be processed to move to the right implemented as the metaverse environment, and the image may be processed to move to the left even in the image of the screen implemented in the metaverse environment.

The operating device 300 is a device worn by the patient and generates an operating signal for a command according to the patient's manipulation, and may be electrically connected to the apparatus 400.

The operating device 300 is worn on the patient's hand to interact on a screen implemented as a metaverse environment, and may be provided as, for example, VR/AR gloves that track the patient's motion, provide physical feedback, and provide feedback for tactile sensation.

The VR/AR gloves tracks motions of a finger, a hand, and a wrist of a patient and implements the motion images on the VR/AR, expresses the hardness of an object in the VR/AR by applying a tensile force of a preset magnitude to each finger, and expresses a touch through a vibration sensor installed on each finger. In the present invention, when the patient uses VR/AR gloves to generate an operating signal in order to interact in a metaverse-based non-face-to-face medical service may be provided through the operating signal.

The apparatus 400 may be a self-managed server owned by a person or organization providing a service using the apparatus 400, may be a cloud server, or may be a peer-to-peer (P2P) set of distributed nodes. The apparatus 400 may be configured to perform all or some of a computational function, a storage/reference function, an input/output function, and a control function of a typical computer.

The apparatus 400 may be configured to communicate with the measuring device 100 in a wired or wireless manner, and may acquire measurement information generated by measuring the health state of the patient from the measuring device 100 to determine the health state of the patient and control the overall operation of the measuring device 100.

The apparatus 400 may be configured to communicate with the output device 200 in a wired or wireless manner, may control which information is to be displayed on the screen of the output device 200, and may control an overall operation of the output device 200.

The apparatus 400 may be configured to communicate with the operating device 300 in a wired or wireless manner, and may acquire an operating signal from the operating device 300 to recognize a patient manipulation, and may control an overall operation of the operating device 300.

The apparatus 400 may provide a metaverse-based healthcare platform so as to enable non-face-to-face diagnosis and self-management in a metaverse environment.

Meanwhile, the measuring device 100, the output device 200, and the operating device 300 may be provided in a diagnostic booth. A detailed description related to the diagnostic booth will be described below with reference to FIGS. 2A-2D.

FIGS. 2A-2D are diagrams for describing a diagnostic booth according to an embodiment.

First, the diagnostic booth is a facility for providing diagnosis and health management in a non-face-to-face environment to maximize the use of the metaverse healthcare platform, and may be configured to communicate with the apparatus 400 in a wired or wireless manner.

As shown in (a) of FIG. 2, the diagnostic booth may be largely composed of a chair, an interior, and an exterior.

The chair of the diagnostic booth may be configured to enable the use of the metaverse healthcare platform. The interior of the diagnostic booth may be configured to respond to infection by using a negative pressure system so that air inside thereof does not remain, and to allow the spray sterilization and the UV sterilization to be automatically performed for a next person. The exterior of the diagnostic booth is lightweight and easy to install, thereby being easily and quickly installed in a small space, and may be manufactured and configured to be easily used even at home.

As shown in (b) of FIG. 2, the interior of the diagnostic booth may be composed of equipment necessary for using the metaverse healthcare platform, such as chairs and personal mobile equipment, industrial scales, negative pressure equipment, sensors, observation equipment, touch monitors, VR equipment, and the like.

As shown in (c) of FIG. 2, the diagnostic booth may be configured to be easily installed to fit a non-face-to-face environment in general medical institutions and homes.

The diagnostic booth may be optimized and configured to enable use of the metaverse healthcare platform.

As shown in (d) of FIG. 2, the diagnostic booth may be equipped with self-blood collection, a blood collection assistance, a needleless syringe, an automatic blood collection device, a self-injector, an infectious disease self-test device, a self-vaccine syringe, a self-personal genetic test, personal genetic disease analysis SW, a blood glucose meter, a height meter, a blood pressure meter, an input device for the visually impaired, an assistant, body fat meter, etc. may be installed as standard or as an option. The various devices installed in the diagnostic booth may be utilized as the measuring device 100.

Figure 3A:
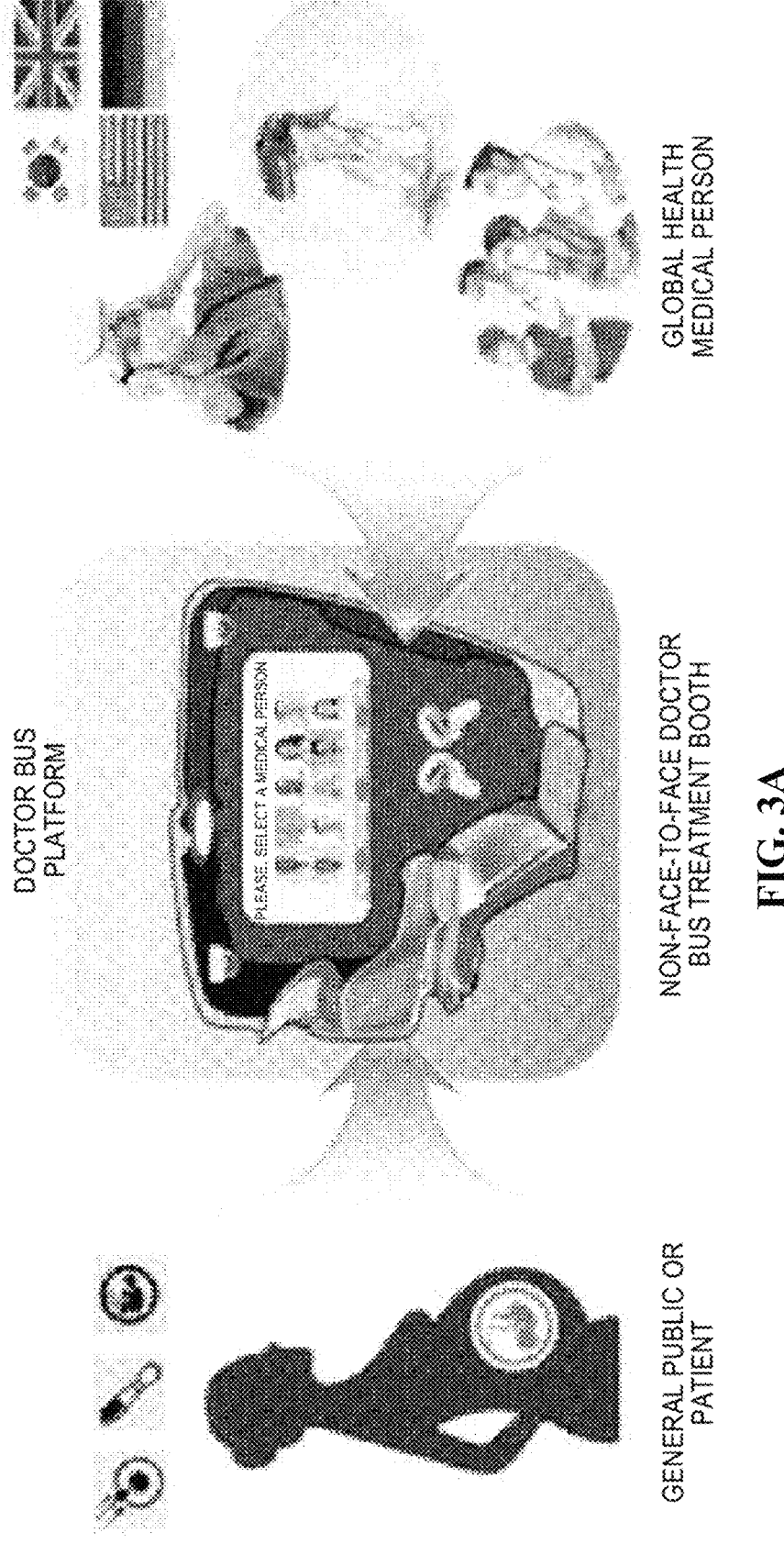
FIGS. 3A-3C are diagrams for describing a metaverse healthcare platform according to an embodiment.
Figure 3B:
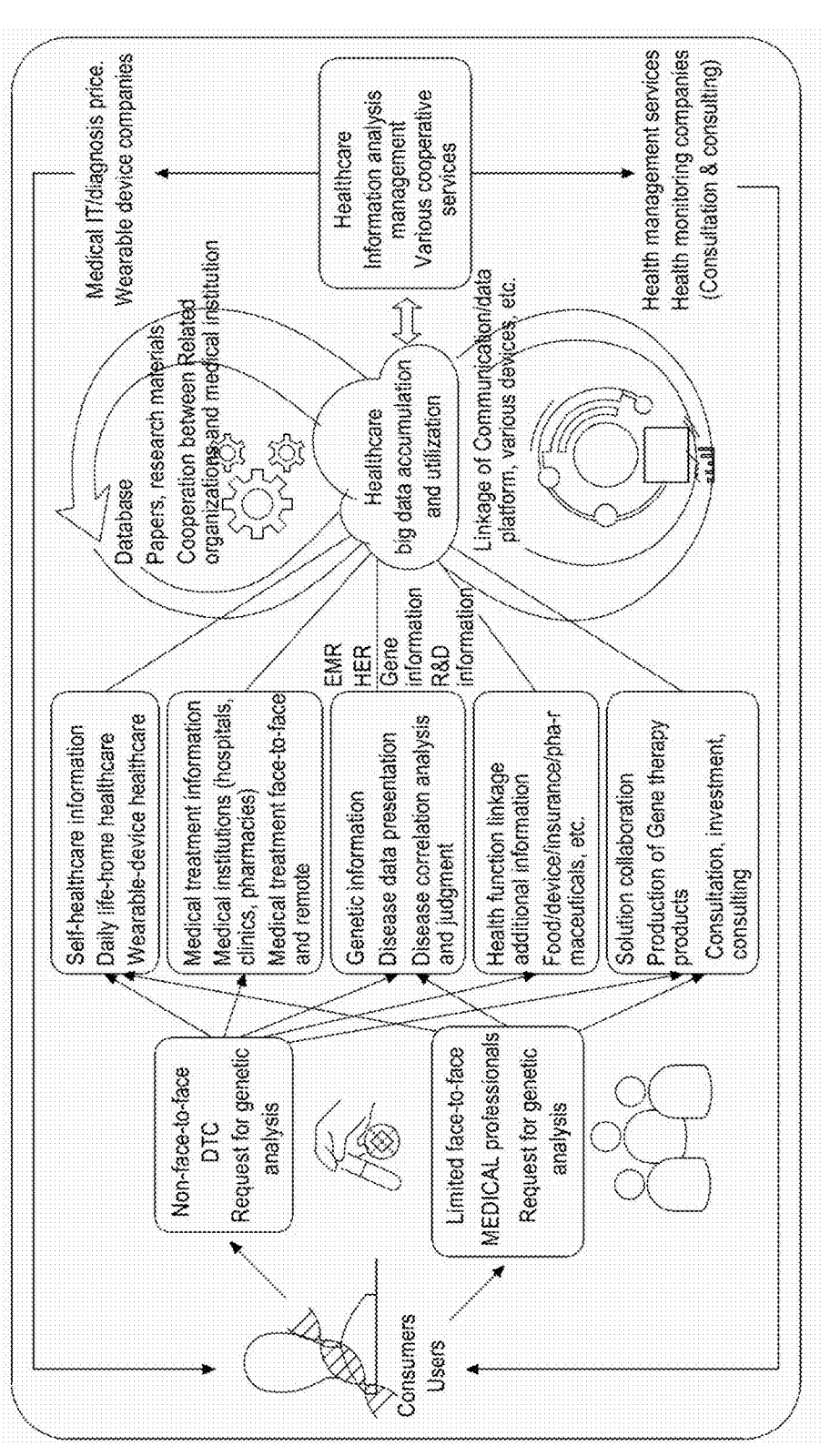
Figure 3C:
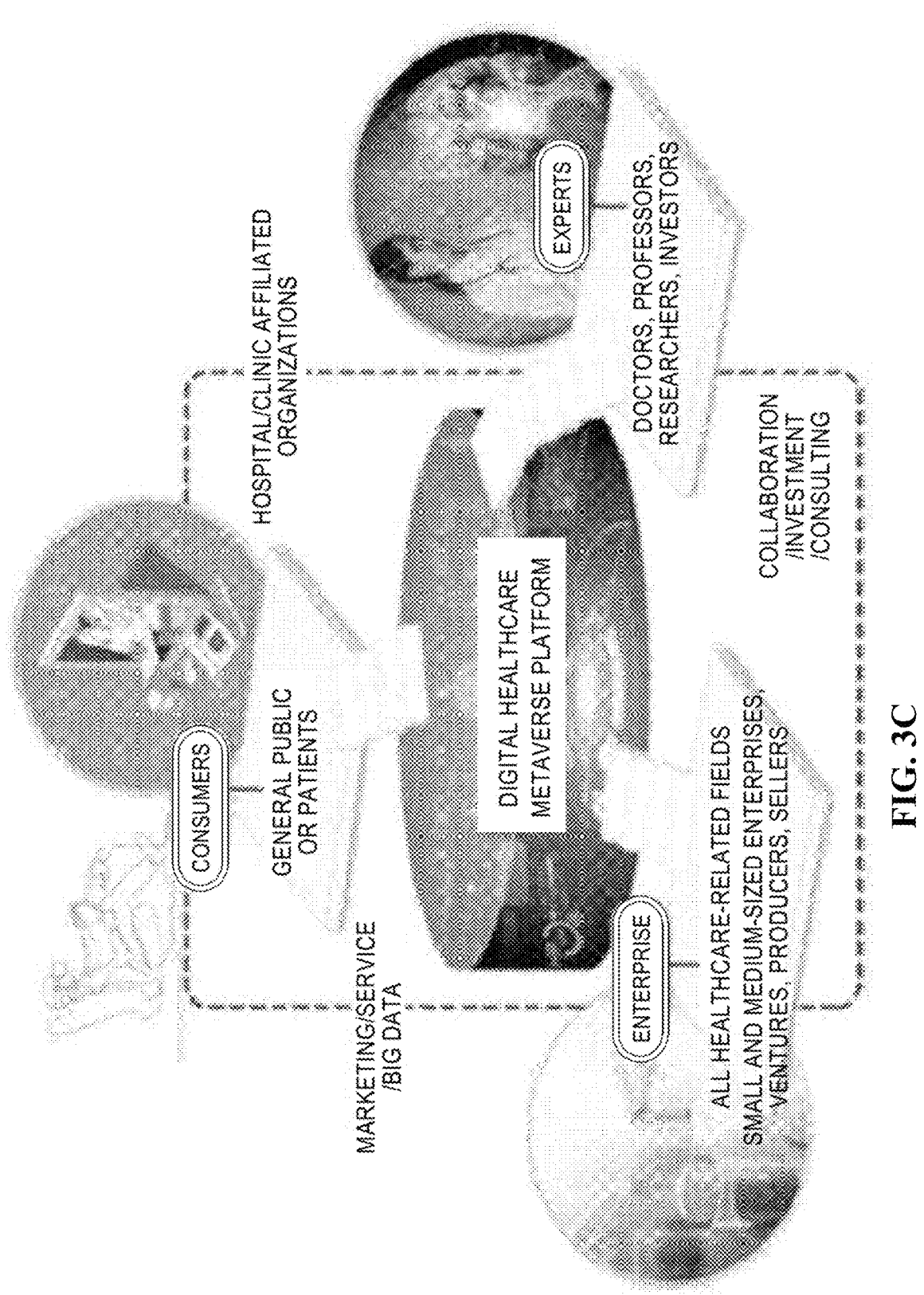

FIGS. 3A-3C are diagrams for describing a metaverse healthcare platform according to an embodiment.

First, as shown in (a) of FIG. 3, in the diagnostic booth, a network may be configured so as to enable a 24-hour global healthcare service to be used through the metaverse healthcare platform. In this case, a function thereof may be limited according to a country and a region where the diagnostic booth is installed.

As shown in (b) of FIG. 3, self-health management information, treatment information, genome information, health function-linked additional information, information acquired through solution collaboration, etc. may be collected through non-face-to-face or limited face-to-face meetings on the metaverse healthcare platform, and accumulated and utilized as big data, and through this, information analysis of health care and provision of various collaboration services may be possible.

As shown in (c) of FIG. 3, the metaverse healthcare platform is an online system for mediating transactions between companies related to all healthcare fields without restrictions of time, space, and money.

The configuration of the metaverse healthcare platform is divided into groups such as experts, enterprises, consumers, etc. The expert group is a group that directly leads healthcare such as doctors, professors, researchers, investors, etc., the entrepreneur group is a group that forms a healthcare market with equipment, design, facilities, consulting, manufacturing, and sellers in all fields related to healthcare, and the consumer group is a group of healthcare industry buyers, either general public or patients, who participate in the platform with a demand for personalized healthcare services.

The business structure of the metaverse healthcare platform may be divided into paid support services through various industrial, academic, research, and hospital services within the platform, main support services through a self-development product of the company operating the platform, and free support services that provide communities and simple support services free of charge.

A company that provides services using the apparatus 400 may be responsible for the operation and maintenance of the metaverse healthcare platform, and therapeutic drug developers (hospitals, research institutes, enterprise research institutes), investors, equipment companies, design/equipment companies (including consulting), sellers (pharmaceutical enterprises), contract manufacturing organization (CMO) enterprises, patients (patients with hereditary or non-hereditary diseases), the general public (general public requiring regular checkups or daily health management), etc. may participate in the platform, so that the metaverse healthcare platform may be operated.

Figure 4:
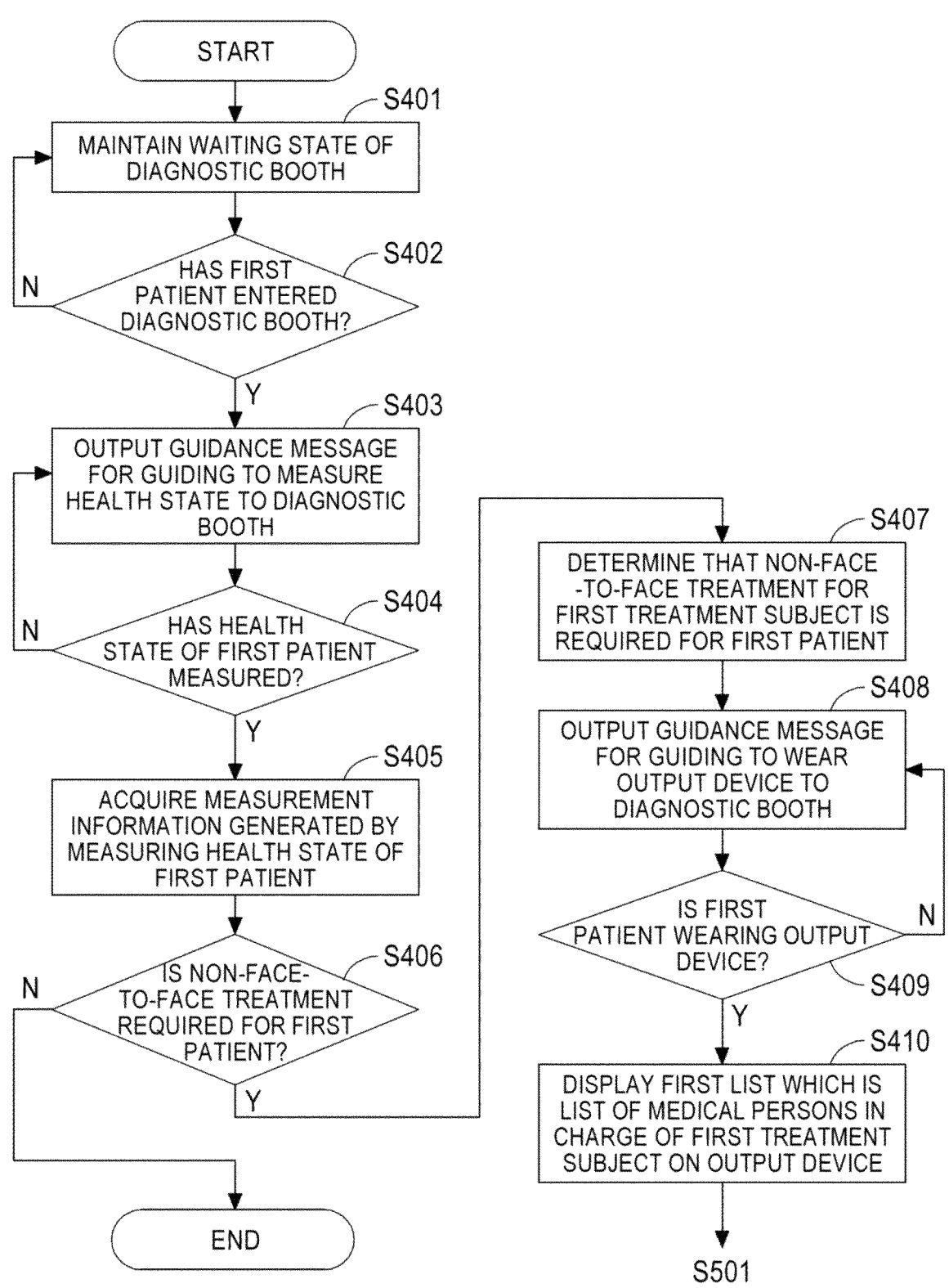
FIG. 4 is a flowchart for describing a process of accessing a metaverse healthcare platform according to an embodiment.

FIG. 4 is a flowchart for describing a process of accessing a metaverse healthcare platform according to an embodiment.

Referring to FIG. 4, first, at step S401, the apparatus 400 may set a state of the diagnostic booth to a waiting state and maintain the waiting state until a patient enters the diagnostic booth.

At step S402, the apparatus 400 may check whether a first patient has entered the diagnostic booth. In this case, when the entrance door of the diagnostic booth is opened, the apparatus 400 may check that the first patient has entered the diagnostic booth, and may also analyze image information obtained by photographing the inside of the diagnostic booth to check that the first patient has entered the diagnostic booth.

When it is checked that the first patient has not entered the diagnostic booth at step S402, the process returns to step S401 and the apparatus 400 may continue to maintain the waiting state of the diagnostic booth.

When it is checked that the first patient has entered the diagnostic booth at step S402, the apparatus 400 may output a guidance message for guiding to measure the health state to the diagnostic booth at step S403. In this case, the apparatus 400 may control an operation of a speaker installed in the diagnostic booth so that the guidance message for guiding to measure the health state is output through the speaker. Here, the guidance message for guiding to measure the health state may include a message for guiding the introduction, usage, etc. of the measuring device 100 which is provided in the diagnostic booth and measures the health state.

At step S404, the apparatus 400 may check whether the first patient has measured the health state of the first patient through the measuring device 100. In this case, when acquiring a measurement start signal indicating that the measurement has started from the measuring device 100, the apparatus 400 may check that the first patient is measuring the health state of the first patient through the measuring device 100.

When it is not checked that the first patient has measured the health state of the first patient through the measuring device 100 after a preset time elapses at step S404, the process returns to step S403 and the apparatus 400 may output a guidance message for guiding to measure the health state to the diagnostic booth again.

When it is checked that the first patient has measured the health state of the first patient through the measuring device 100 at step S404, the apparatus 400 may acquire measurement information generated by measuring the health state of the first patient from the measuring device 100 at step S405. Here, the measurement information may be generated differently depending on a type of the measuring device 100.

For example, when the measuring device 100 is a blood pressure measuring device, the first patient may measure a blood pressure of the first patient through the measuring device 100, the measuring device 100 may measure the blood pressure of the first patient and generate measurement information indicating the blood pressure of the first patient, and the apparatus 400 may acquire the measurement information indicating the blood pressure of the first patient from the measuring device 100.

At step S406, the apparatus 400 may determine whether non-face-to-face treatment is required for the first patient, based on the measurement information. A detailed description of the contents of determining whether the non-face-to-face treatment is required will be described below with reference to FIG. 7.

When it is determined that the non-face-to-face treatment is not required for the first patient at step S406, the apparatus 400 may output a guidance message, which guides the patient to leave the diagnosis booth, because there is no abnormality in the patient's health condition. In this case, the apparatus 400 may control the operation of the speaker installed in the diagnostic booth so that the guidance message for guiding the patient to leave the diagnostic booth is output through the speaker.

When it is determined that the non-face-to-face treatment is required for the first patient at step S406, the apparatus 400 may determine that non-face-to-face treatment for a first treatment subject is required for the first patient, based on the measurement information, at step S407.

For example, when the blood pressure of the first patient is analyzed to be high blood pressure through the measurement information, the apparatus 400 may set a department of vascular medicine in charge of high blood pressure treatment as the first treatment subject, and determine that the non-face-to-face treatment for the department of vascular medicine is required for the first patient.

At step S408, the apparatus 400 may output a guidance message for guiding to wear the output device 200 to the diagnostic booth. In this case, the apparatus 400 may control the operation of the speaker installed in the diagnostic booth so that the guidance message for guiding to wear the output device 200 is output through the speaker.

At step S409, the apparatus 400 may check whether the first patient wears the output device 200. In this case, when a detection signal is acquired from a sensor attached to the output device 200, the apparatus 400 may check that the first patient wears the output device 200.

When it is checked that the first patient has not worn the output device 200 after a preset time elapses at step S409, the process returns to step S408, and the apparatus 400 may output a guidance message for guiding to wear the output device 200 to the diagnostic booth again.

When it is checked that the first patient wears the output device 200 at step S409, the apparatus 400 may perform control so that a first list, which is a list of medical persons in charge of the first treatment subject, is displayed on the output device 200 at step S410. That is, when it is checked that the first patient wears the output device 200, the apparatus 400 may perform control so that the first list is displayed on a medical person selection screen from which a medical person can be selected.

After step S409, step S501 may be performed, and a detailed description related thereto will be described below with reference to FIG. 5.

Figure 5:
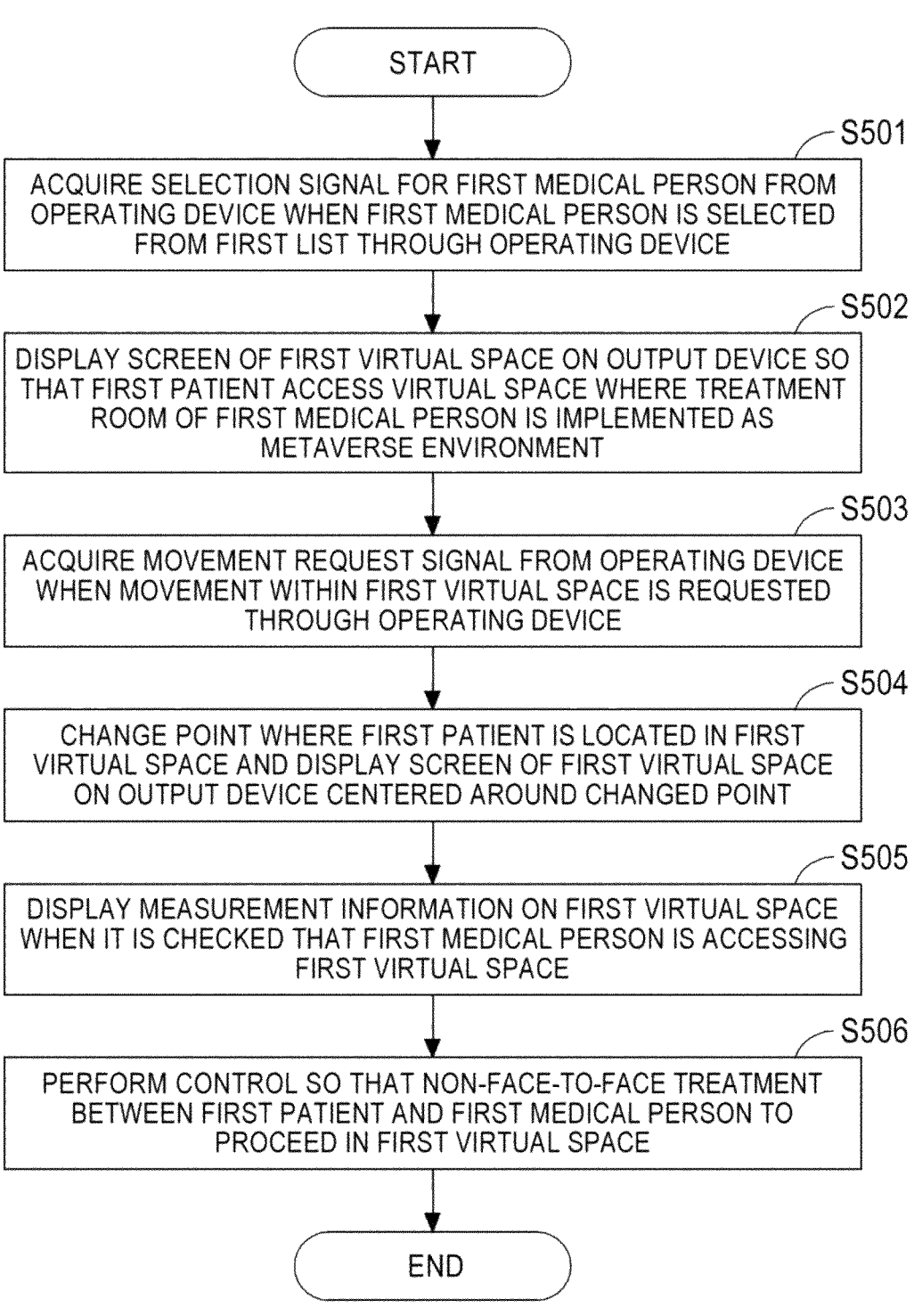
FIG. 5 is a flowchart for describing a process of providing a metaverse healthcare platform service for non-face-to-face diagnosis and self-management according to an embodiment.

FIG. 5 is a flowchart for describing a process of providing a metaverse healthcare platform service for non-face-to-face diagnosis and self-management according to an embodiment.

Referring to FIG. 5, first, at step S501, when a first patient wears the operating device 300, if the first medical person is selected from the first list through the operating device 300, the apparatus 400 may acquire a selection signal for a first medical person from the operating device 300.

At step S502, when it is checked that the first medical person is selected from the first list displayed on a medical person selection screen through the selection signal for the first medical person, the apparatus 400 may perform control so that a screen of a first virtual space corresponding to the treatment room of the first medical person is displayed on the output device 200.

To this end, each treatment room provided for each medical person is implemented as a metaverse environment, and the first virtual space may mean a virtual space where the treatment room of the first medical person is implemented as a metaverse environment.

The apparatus 400 may perform control so that the screen of the first virtual space is displayed on the output device 200 worn by the first patient so as to allow the first patient to access the first virtual space, and the first patient may feel the same experience as accessing the first virtual space through the screen of the first virtual space displayed on the output device 200.

At step S503, when movement within the first virtual space is requested through the operating device 300, the apparatus 400 may acquire a movement request signal from the operating device 300.

At step S504, when it is checked that that movement within the first virtual space is requested through a movement request signal, the apparatus 400 may perform control so that a point where the first patient is located in the first virtual space is changed and the screen of the first virtual space is displayed with the changed point as a center change on the output device.

For example, when the first patient accesses the first virtual space, the first patient may be located at a first point within the first virtual space, and the apparatus 400 may perform control so that the screen of the first virtual space is displayed with the first point as a center on the output device 200.

After that, when the first patient moves to a second point within the first virtual space due to the movement request within the first virtual space, the apparatus 400 may perform control so that the screen of the first virtual space centered on the second point is displayed with the second point as a center on the output device 200.

At step S505, when it is checked that the first medical person is accessing the first virtual space, the apparatus 400 may perform control so that the measurement information is displayed on the first virtual space.

When the first patient is accessing the first virtual space but the first medical person is not accessing the first virtual space, the apparatus 400 may transmit a notification message notifying that a patient is waiting in the first virtual space to the first medical person terminal to which a first medical person account is logged in, thereby inducing the first medical person to access the first virtual space.

In a state where the first patient wears the output device 200 is accessing the first virtual space, when the first medical person wearing another output device 200 accesses the first virtual space, the apparatus 400 may check that the first patient and the first medical person have accessed simultaneously the first virtual space, perform control so that the character or avatar of the first medical person is displayed on the output device 200 worn by the first patient, and perform control so that the character or avatar of the first patient is displayed on the output device 200 the output device 200 worn by the first medical person.

When the character or avatar of the first patient is displayed on the output device 200 worn by the first medical person, the apparatus 400 may perform control so that measurement information generated by measuring the health state of the first patient is displayed together with the character or avatar of the first patient.

In addition, when the character or avatar of the first medical person is displayed on the output device 200 worn by the first patient, the apparatus 400 may perform control so that the measurement information generated by measuring the health state of the first patient is displayed on the first virtual space.

At step S506, the apparatus 400 may perform control so that the non-face-to-face treatment between the first patient and the first medical person proceeds in the first virtual space. In this case, the apparatus 400 may provide a service that allows the first patient and the first medical person to actually talk.

Specifically, when a voice of the first patient is input through a microphone installed in the output device 200 worn by the first patient, the apparatus 400 may perform control so that the voice of the first patient is output through a speaker installed in the output device 200 worn by the first medical person and when a voice of the first medical person is input through the microphone installed in the output device 200 worn by the first medical person, the apparatus 400 may perform control so that the voice of the first medical person is output through the speaker installed in the output device 200 worn by the first patient, thereby providing a service in which the first patient and the first medical person may actually talk in the first virtual space.

Figure 6:
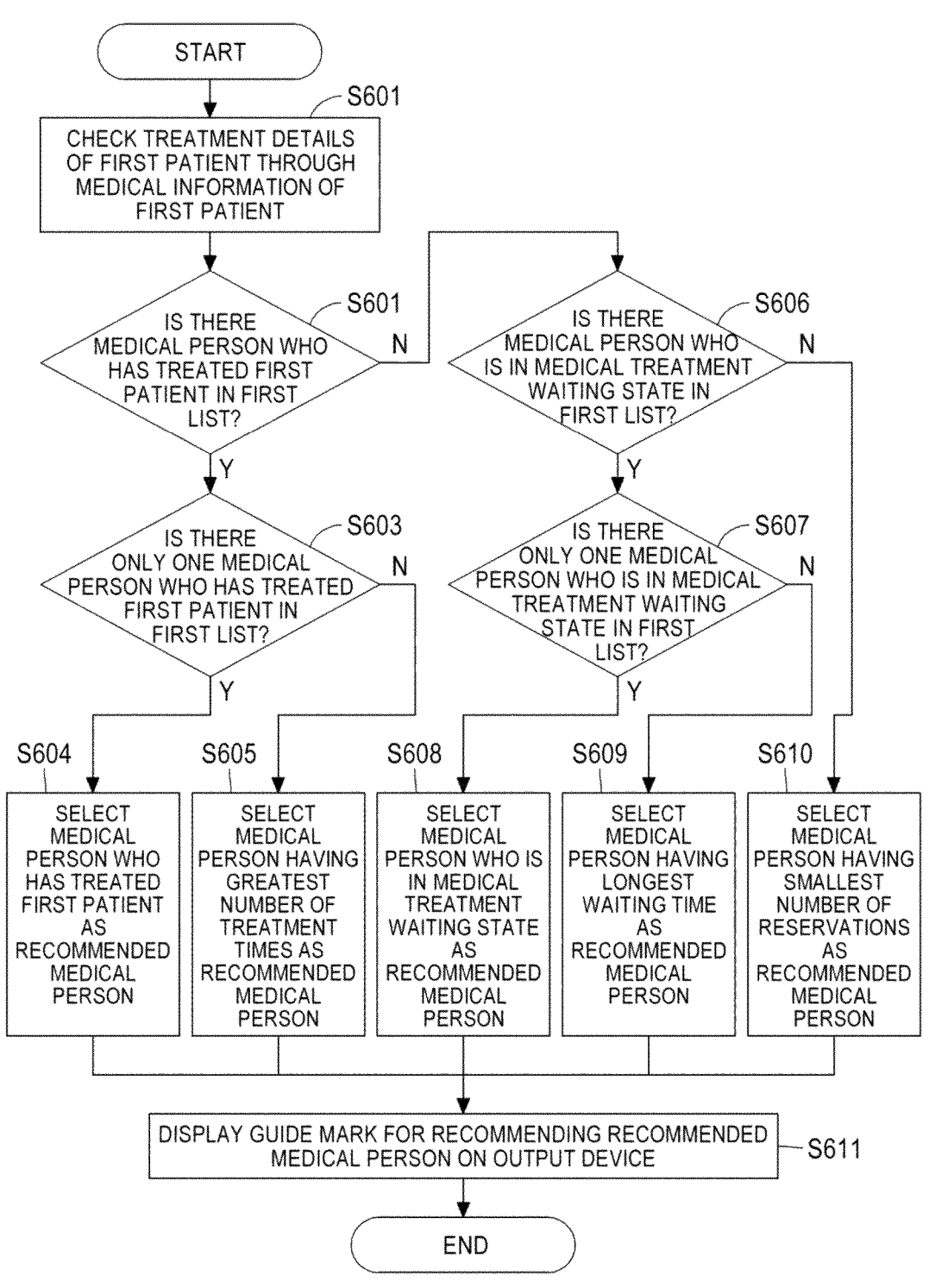
FIG. 6 is a flowchart for describing a process of recommending a medical person to a patient according to an embodiment.

FIG. 6 is a flowchart for describing a process of recommending a medical person to a patient according to an embodiment.

Referring to FIG. 6, first, at step S601, the apparatus 400 may check treatment details of the first patient through medical information of the first patient. To this end, a database of the apparatus 400 stores medical information classified for each patient, and the medical information may include information such as checkup details, diagnosis details, treatment details, examination details, prescription details, and cure details, etc.

That is, the apparatus 400 may acquire the medical information of the first patient by inquiring the medical information stored in the database, and may check the treatment details of the first patient from the medical information of the first patient. Here, the treatment details include information about a date of treatment, treatment content, a medical person who has performed the treatment, etc.

At step S602, the apparatus 400 may check whether there is a medical person who has treated the first patient among the medical persons included in the first list, based on the treatment details of the first patient. In this case, the apparatus 400 may check the medical person who has performed the treatment of the first patient in the treatment details of the first patient, compare the medical person who has performed the treatment of the first patient with the first list, and check whether there is a medical person who has treated the first patient among the medical persons included in the first list.

When it is checked that there is a medical person who has treated the first patient among the medical persons included in the first list at step S602, the apparatus 400 may check whether there is only one medical person who has treated the first patient among the medical persons included in the first list at step S603.

When it is checked that there is only one medical person who has treated the first patient among the medical persons included in the first list at step S603, the apparatus 400 may select a medical person who has treated the first patient as a recommended medical person at step S604.

When it is checked that there are two or more medical persons who have treated the first patient, rather than just one, among the medical persons included in the first list at step S603, the apparatus 400 may select, as a recommended medical person, a medical person having the greatest number of treatment times, which is the number of times that the first patient has been treated, among medical persons who have treated the first patient at step S605.

When it is checked that there is no medical person who has treated the first patient among the medical persons included in the first list at step S602, the apparatus 400 may check whether there is a medical person who is in a treatment waiting state among the medical persons included in the first list at step S606. Here, the treatment waiting state may refer to a state in which a medical person is accessing alone the treatment room implemented as a metaverse environment and is in a waiting state in which the medical person is waiting for a patient.

When it is checked that there is a medical person who is in the treatment waiting state among the medical persons included in the first list at step S606, the apparatus 400 may check whether there is only one medical person who is in the treatment waiting state among the medical persons included in the first list at step S607.

When it is checked that there is only one medical person who is in the treatment waiting state among the medical persons included in the first list at step S607, the apparatus 400 may select the medical person who is in the treatment waiting state as a recommended medical person at step S608.

When it is checked that there are two or more medical persons who are in the treatment waiting state, rather than just one, among the medical persons included in the first list at step S607, the apparatus 400 may select, as a recommended medical person, a medical person having the longest waiting time among the medical persons who are in the treatment waiting state at step S609. That is, the apparatus 400 may select, as the recommended medical person the medical person who has maintained the longest treatment waiting state among the medical persons who are in the treatment waiting state.

When it is checked that there is no medical person who is in the treatment waiting state among the medical persons included in the first list at step S606, the apparatus 400 may select, as the recommended medical person, the medical person having the smallest number of reservations among the medical persons included in the first list.

At step S611, when the recommended medical person is selected from the first list, the apparatus 400 may perform control so that a guide mark for recommending the recommended medical person is displayed on the output device 200 so as to be overlapped with the first list.

For example, when the first medical person is selected as the recommended medical person from the first list, if the first list is displayed on the output device 200, the apparatus 400 may perform control so that a guide mark in the shape of an arrow for recommending the first medical person is displayed on the output device 200 together with the first list.

Figure 7:
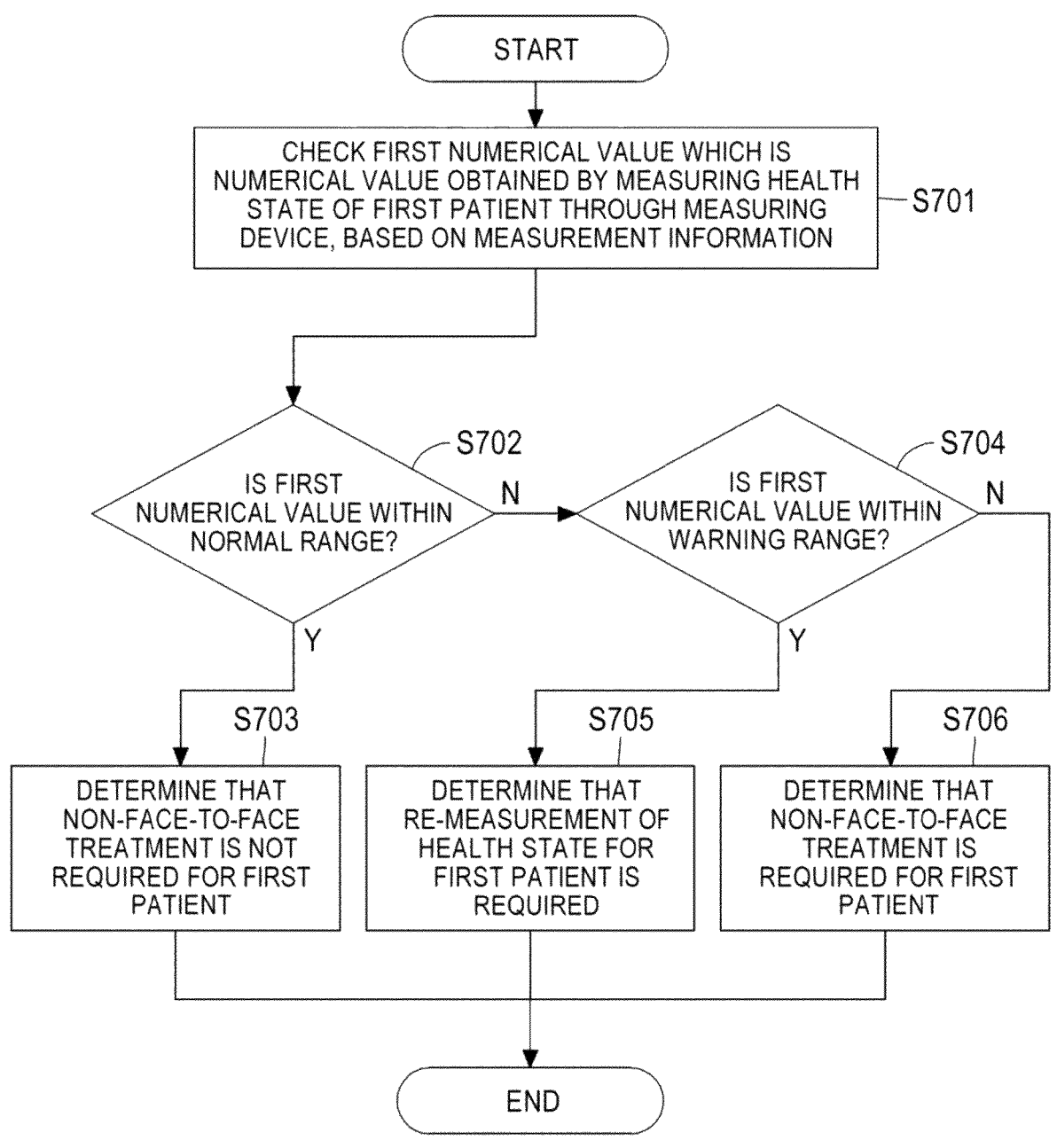
FIG. 7 is a flowchart for describing a process of determining whether non-face-to-face treatment is required according to an embodiment.

FIG. 7 is a flowchart for describing a process for determining whether a non-face-to-face treatment is required according to an embodiment.

Referring to FIG. 7, first, at step S701, the apparatus 400 may check a first numerical value, which is a numerical value obtained by measuring the health state of the first patient through the measuring device 100, based on measurement information.

For example, when the measuring device 100 is a heart rate measuring device, the apparatus 400 may acquire measurement information indicating a heart rate of the first patient from the measuring device 100, and may check the first numerical value, which is a numerical value obtained by measuring the heart rate of the first patient, based on the measurement information.

At step S702, the apparatus 400 may check whether the first numerical value is within a normal range. Here, the normal range may be set differently depending on a type of the measuring device 100. For example, when the first numerical value is a heart rate, the normal range may be set from 60 to 70.

When it is checked that the first numerical value is within the normal range at step S702, the apparatus 400 may determine that the non-face-to-face treatment is not required for the first patient at step S703.

When it is checked that the first numerical value is out of the normal range at step S702, the apparatus 400 may check whether the first numerical value is within a warning range at step S704. Here, the warning range may be set differently depending on the type of the measuring device 100, and may be set to a range wider than the normal range. For example, when the first numerical value is the heart rate, the normal range may be set from 60 to 70, and the warning range may be set from 50 to 80.

When it is checked that the first numerical value is within the warning range at step S704, the apparatus 400 may determine that re-measurement of the health state of the first patient is required at step S705.

After that, the apparatus 400 may check a 1-1 numerical value, which is a numerical value obtained by re-measuring the health state of the first patient through the measuring device 100, and when it is checked that the 1-1 numerical value is out of the normal range and within the warning range, the apparatus 400 may determine that the non-face-to-face treatment is required for the first patient.

When it is checked that the first numerical value is out of the warning range at step S704, the apparatus 400 may determine that the non-face-to-face treatment is required for the first patient at step S706.

Figure 8:
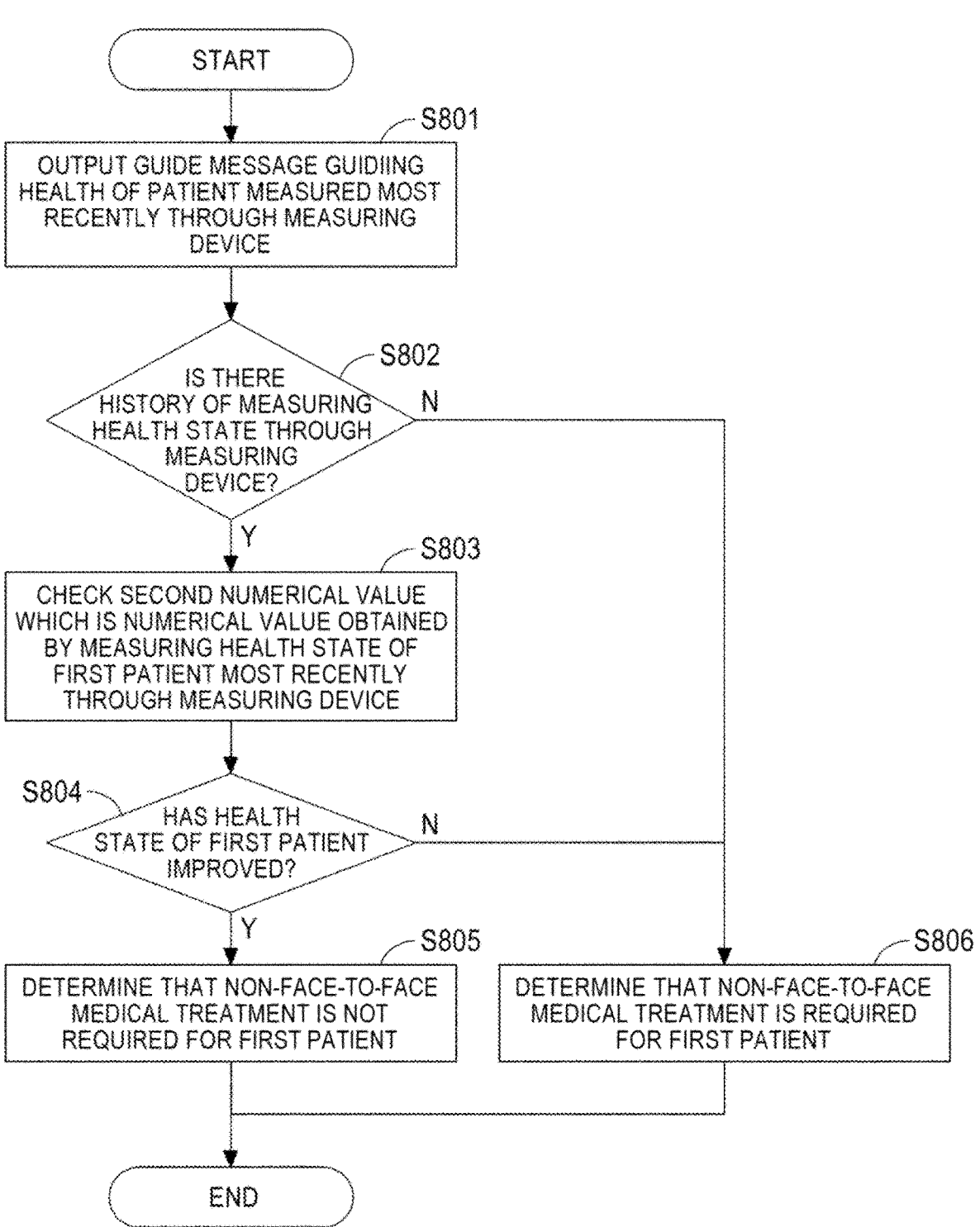
FIG. 8 is a flowchart for describing a process of determining whether non-face-to-face treatment is required through examination details according to an embodiment.

FIG. 8 is a flowchart for describing a process for determining whether non-face-to-face treatment is required through examination details according to an embodiment.

Referring to FIG. 8, first, at step S801, the apparatus 400 may check the examination details of the first patient through medical information of the first patient.

That is, the apparatus 400 may acquire the medical information of the first patient by inquiring the medical information stored in the database, and may check the examination details of the first patient in the medical information of the first patient. Here, the examination details include information about an examination date, an examination result, and a measuring device that has performed the examination.

At step S802, the apparatus 400 may check whether there is a history of measuring the health state through the measuring device 100 based on the examination details of the first patient.

For example, when the measuring device 100 is a heart rate measuring device, the apparatus 400 may check whether there is a history of measuring the heart rate through the heart rate measuring device in the examination details of the first patient.

When it is checked that there is no history of measuring the health state through the measuring device 100 at step S802, the apparatus 400 may determine that the non-face-to-face treatment is required for the first patient at step S806.

That is, when the apparatus 400 measures the health state through the measuring device 100, but it is checked that the first numerical value is out of the warning range, the apparatus 400 may determine that the non-face-to-face treatment is required for the first patient.

When it is checked that there is the history of measuring the health state through the measuring device 100 at step S802, the apparatus 400 may check a second numerical value, which is a numerical value obtained by measuring the health state of the first patient most recently through the measuring device 100, based on the examination details of the first patient at step S803.

That is, the apparatus 400 may check the examination date of the examination performed most recently in the examination details of the first patient, and check the examination result of the checked examination date as the second numerical value.

At step S804, the apparatus 400 may compare the first numerical value and the second value to determine whether the health state of the first patient has improved.

For example, when the first numerical value and the second numerical value are systolic blood pressures, if it is checked that the first numerical value is 140 mmHg and the second numerical value is 150 mmHg as a result of comparing the first numerical value and the second numerical value, the apparatus 400 may determine that the health state of the first patient has improved from the high blood pressure state because the first numerical value, which is the current measurement numerical value, is lower than the second value, which is the past measurement numerical value.

In addition, when the first numerical value and the second numerical value are systolic blood pressures, if it is checked that the first numerical value is 150 mmHg and the second numerical value is 140 mmHg as a result of comparing the first numerical value and the second numerical value, the apparatus 400 may determine that the health state of the first patient is degraded in the high blood pressure state because the first numerical value, which is the current measurement numerical value, is higher than the second value, which is the past measurement numerical value.

In addition, when the first numerical value and the second numerical value are systolic blood pressure, if it is checked that the first numerical value is 70 mmHg and the second numerical value is 60 mmHg, the apparatus 400 may determine that the health state of the first patient has improved from the low blood pressure state because the first numerical value, which is the current measurement numerical value, is higher than the second value, which is the past measurement numerical value.

In addition, when the first numerical value and the second numerical value are systolic blood pressure, if it is checked that the first numerical value is 60 mmHg and the second numerical value is 70 mmHg, the apparatus 400 may determine that the health state of the first patient is degraded from the low blood pressure state because the first numerical value, which is the current measurement numerical value, is lower than the second value, which is the past measurement numerical value, and thus.

That is, the apparatus 400 may compare the first numerical value and the second numerical value according to the types of the first numerical value and the second numerical value to determine whether the current health state of the first patient has improved than the past health state.

When it is determined that the health state of the first patient has improved at step S804, the apparatus 400 may determine that the non-face-to-face treatment is not required for the first patient at step S804.

That is, although it is checked that the first numerical value deviates from the warning range, when it is determined that the health state of the first patient has improved as a result of comparing the first numerical value and the second numerical value, the apparatus 400 may determine that the non-face-to-face treatment is not required for the first patient.

When it is determined that the health condition of the first patient has not improved at step S804, the apparatus 400 may determine that the non-face-to-face treatment is required for the first patient at step S806.

Figure 9:
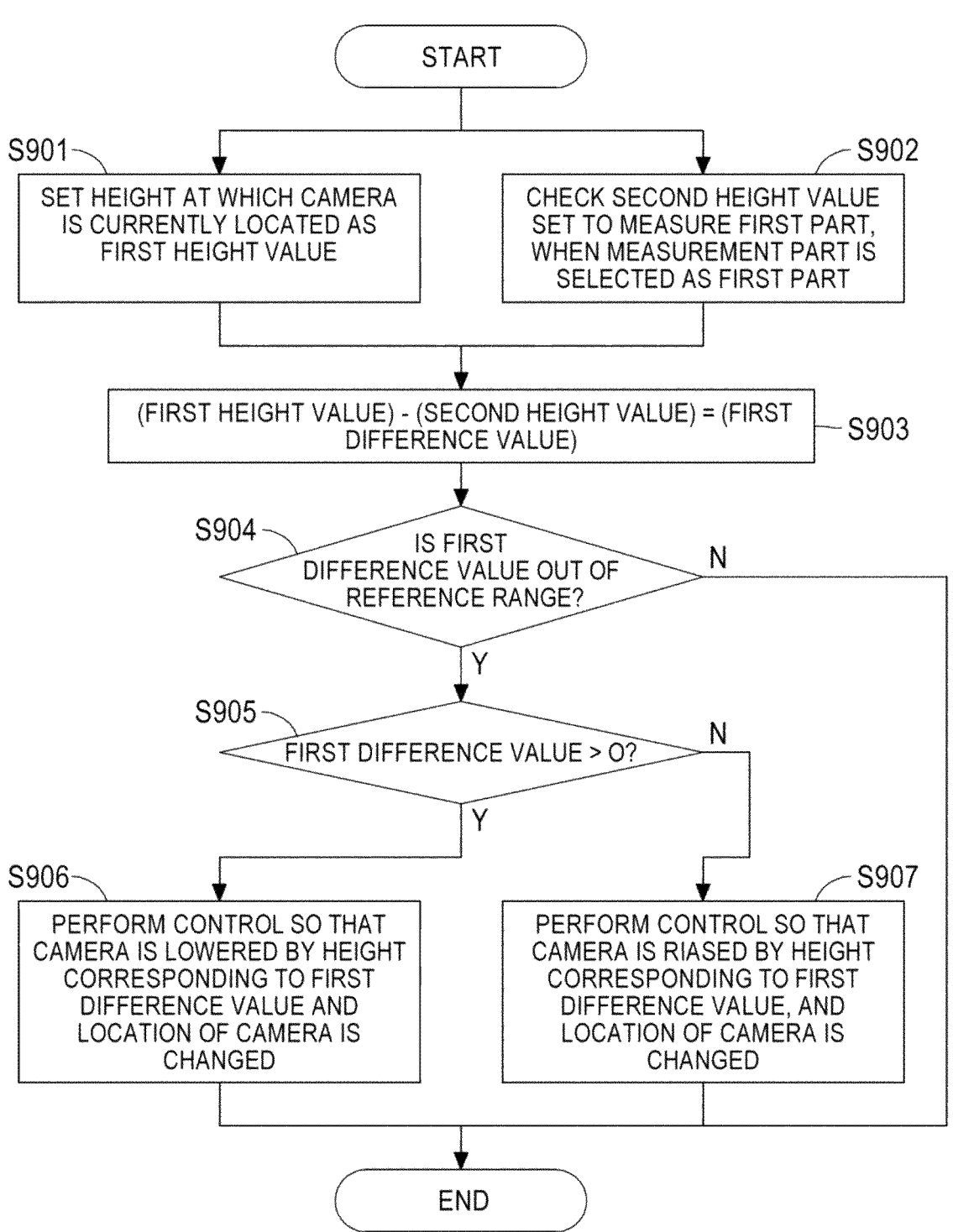
FIG. 9 is a flowchart for describing a process of setting a camera height according to a measurement part according to an embodiment.

FIG. 9 is a flowchart for describing a process of setting a camera height according to a measurement part according to an embodiment.

First, when the measuring device 100 is a first measuring device that measures blood flow, the apparatus 400 may be configured to communicate with the first measuring device wirelessly or in a wired manner, and may control the overall operation of the first measuring device.

According to an embodiment, the first measurement device may include a camera, a monitor, a support, and a moving wheel.

Specifically, the first measurement device is a laser blood flow meter that measures blood flow in tissues within the human body using a laser, and may be configured to perform all or some of a calculation function, a storage/reference function, an input/output function, and a control function of a general computer.

The camera of the first measuring device may be composed of a laser diode, a diffuser, an NIR camera, a lens, a bandpass filter, etc. The camera of the first measuring device may perform a function of emitting laser light toward a measurement part when the measurement part is located in front of the lens, and receiving, when the emitted laser light is scattered from a surface of the measuring device, the scattered laser light and generating an image through the received laser light.

The monitor of the first measuring device may be configured as a display device that visually displays data. The monitor of the first measuring device may perform a function of displaying an image generated by the camera of the first measuring device on a screen.

The support of the first measurement device may be connected to the camera of the first measuring device and the monitor of the first measuring device, and may be configured as a height adjustment means for adjusting a height at which the camera of the first measurement device and the monitor of the first measurement device are located. That is, the camera of the first measuring device and the monitor of the first measuring device may move up and down through the support of the first measuring device to change the height at which the camera of the first measuring device and the monitor of the first measuring device are located.

The moving wheel of the first measuring device may be connected to the support of the first measuring device and configured as a moving means for moving the first measuring device.

Meanwhile, the first measuring device may be implemented as a laser speckle contrast imaging (LSCI) product, and the LSCI is a laser affected area irradiator that noninvasively or invasively measures a blood flow rate using a laser.

The first measurement device may be used to measure blood flow disorders (thrombus, stenosis, mechanical damage, etc.), or to support an evaluation of the degree thereof, visualize micro-circulating blood perfusion in real time, and provide a means for studying micro-circulating blood flow.

The first measuring device is an LSCI system that may be used to monitor blood flow, and may be implemented as a product that imaging changes in laser speckle.

An LSCI technology is a simple and powerful technique used for imaging the full-field of blood flow, and in which laser speckle may be reconstructed into an image in which the relative velocity of a scatterer may be known by acquiring the degree of contrast of a speckle pattern that changes according to a moving scatterer.

Since the LSCI may be used to monitor the movement of red blood cells, the LSCI may be possible to measure blood flow of tissues such as retina, skin, brain, and the like.

That is, the first measuring device can monitor tissue necrosis and wound parts through the LSCI, and can acquire a blood flow image and monitor blood flow in real time.

Meanwhile, laser speckle is a technology that may be used for deformation and stress analysis, non-destructive inspection, or vibration analysis of an object through non-contact high resolution only with changes in an optical interferometer using a laser.

When the surface of an object is irradiated with light having excellent coherence such as laser light, due to a roughness of the surface of the object, the laser is scattered and interfered to form a spot-like pattern, which is referred to as a speckle pattern. The speckle pattern includes surface deformation information of the object, and information on the surface deformation of the object may be acquired by recording and processing the speckle pattern.

That is, when an object is diffusely irradiated with a laser before deformation of the object, a speckle pattern is formed, and this speckle pattern, which has information on the surface shape of the object, is recorded by an image processing device. When deformation of the object occurs, the speckle pattern changes along with the deformation of the surface of the object, and the speckle pattern after deformation of the object is recorded on the image processing device. In addition, a fringe pattern may be obtained by performing real-time subtraction of the recorded speckle pattern before and after two modifications, and the interval of stripes of the fringe pattern may be related to the deformation of the object. That is, deformation information before and after deformation of the object can be obtained by appropriately processing the interval of the stripes.

As described above, the first measuring device may measure changes in blood flow through a method of measuring the deformation of the object using the laser speckle pattern.

Referring to FIG. 9, at step S901, the apparatus 400 may set a height at which the camera of the first measuring device is currently located as a first height value. In this case, the apparatus 400 may check which portion of the support of the first measuring device the camera of the first measuring device is connected to, and may check the height at which the camera of the first measuring device is currently located, and set the height at which the camera of the first measuring device is currently located as the first height value.

At step S902, when the measurement part is selected as a first part, the apparatus 400 may check a second height value which is set to measure the first part. To this end, information on a height value optimized for measurement for each part is stored in the database of the apparatus 400, and the apparatus 400 may acquire information on the height value of the first part from the database and check the second height value through the acquired information. The selection for the first part may be selected by a button provided on the support of the first measuring device, or may be selected on a touch screen provided on the monitor of the first measuring device.

For example, when the measurement part is selected as the wrist, the apparatus 400 may check the height value which is set for measuring the wrist part as the second height value, and when the measurement part is selected as the ankle, the apparatus 400 may check the height value set for measuring the ankle part as the second height value.

At step S903, the apparatus 400 may calculate a first difference value by subtracting the second height value from the first height value.

At step S904, the apparatus 400 may check whether the first difference value is out of a reference range. Here, the reference range may be set differently depending on the embodiment, and for example, the reference range may be set from −5 cm to 5 cm.

When it is checked that the first difference value is out of the reference range at step S904, the apparatus 400 may check whether the first difference value is greater than 0 at step S905.

When it is checked that the first difference value is greater than 0 at step S905, the apparatus 400 may control the camera of the first measuring device to be lowered by a height corresponding to the first difference value, so that the position of the camera of the first measuring device is changed, at step S906.

For example, when the first height value is 90 cm, the second height value is 80 cm, and the reference range is set from −5 cm to 5 cm, the apparatus 400 may calculate the first difference value as 10 cm. Since it is checked that the first difference value is out of the reference range and greater than 0, the apparatus 400 may control the camera of the first measuring device to be lowered by 10 cm from the current position, so that the position of the camera of the first measuring device is changed.

When it is checked that the first difference value is less than 0 at step S905, the apparatus 400 may control the camera of the first measuring device to be raised by a height corresponding to the first difference value, so that the position of the camera of the first measuring device is changed, at step S907.

For example, when the first height value is 80 cm, the second height value is 90 cm, and the reference range is set from −5 cm to 5 cm, the apparatus 400 may calculate the first difference value as −10 cm. Since it is checked that the first difference value is out of the reference range and is less than 0, the apparatus 400 may control the camera of the first measuring device to be raised by 10 cm from the current position, so that the position of the camera of the first measuring device is changed.

Figure 10:
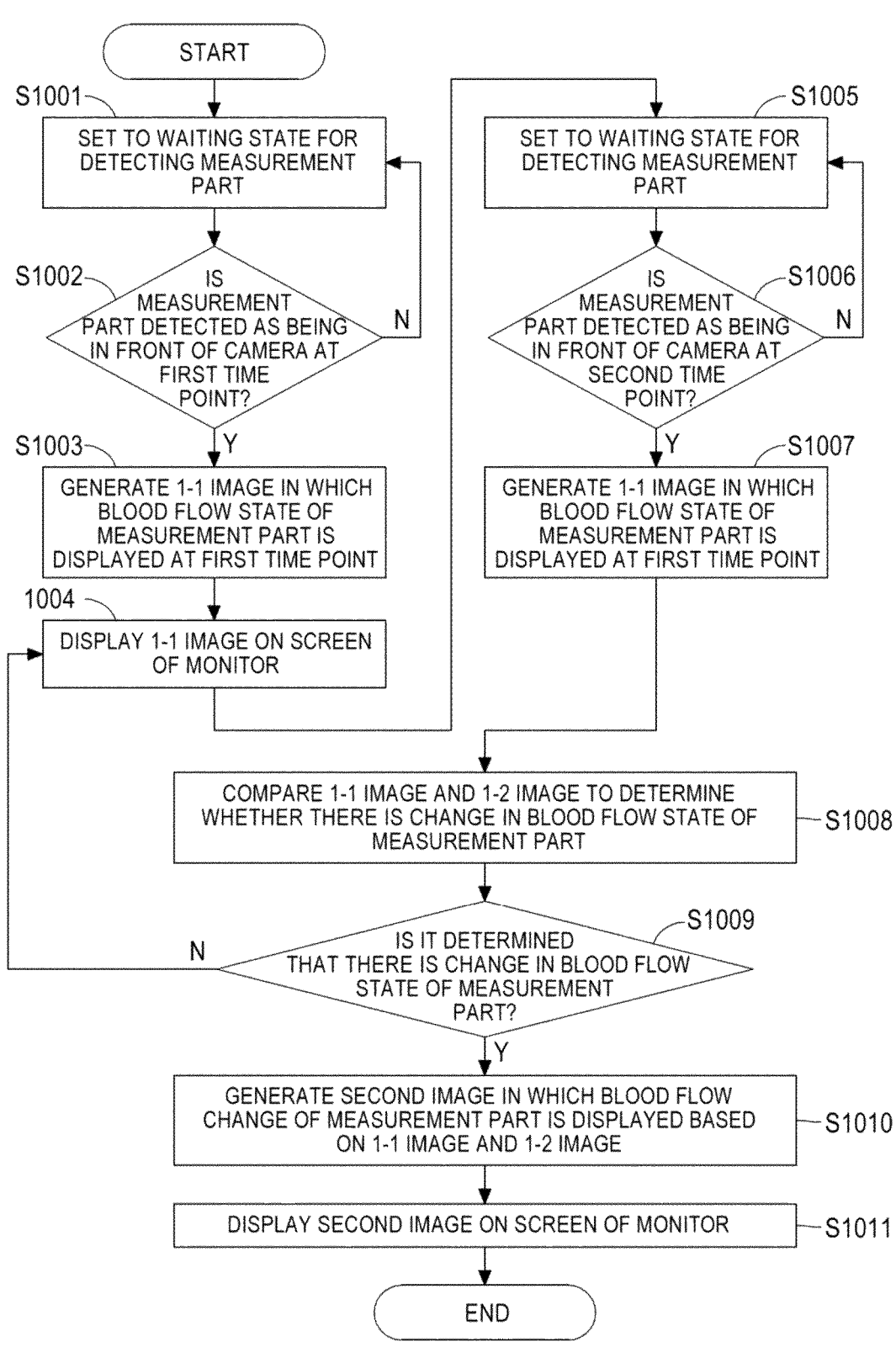
FIG. 10 is a flowchart for describing a process of acquiring an image of a blood flow change measurement result as measurement information according to an embodiment.

FIG. 10 is a flowchart for describing a process of acquiring an image of a blood flow change measurement result as measurement information according to an embodiment.

Referring to FIG. 10, first, at step S1001, the apparatus 400 may be set to a waiting state for detecting a measurement part of a first patient. To this end, the camera of the first measuring device may be equipped with a sensor, and the sensor may be set to a waiting state for detecting whether a measurement part is located in front of the camera of the first measuring device.

At step S1002, the apparatus 400 may check whether the measurement part of the first patient is detected as being in front of the camera of the first measuring device at a first time point.

When the measurement part of the first patient is not detected as being in front of the camera of the first measuring device at step S1002, the process returns to step S1001, and the apparatus 400 may maintain the waiting state for detecting the measurement part of the first patient.

When the measurement part of the first patient is detected as being in front of the camera of the first measuring device at step S1002, the apparatus 400 may generate a 1-1 image showing a blood flow state of the measurement part of the first patient at the first time point at step S1003.

Specifically, when the measurement part of the first patient is detected as being in front of the camera of the first measuring device at the first time point, the apparatus 400 emits laser light to the measurement part of the first patient through the camera of the first measuring device. When the emitted laser light is scattered from the surface of the measurement part of the first patient, the apparatus 400 may generate, using a laser speckle pattern, the 1-1 image showing the blood flow state of the measurement part of the first patient at the first time point.

At step S1004, when the 1-1 image is generated, the apparatus 400 may display the 1-1 image on a screen of the monitor of the first measuring device.

At step S1005, the apparatus 400 may be set to a waiting state for detecting the measurement part of the first patient.

At step S1006, the apparatus 400 may check whether the measurement part of the first patient is detected as being in front of the camera of the first measuring device at a second time point. Here, the second time point may refer to a time point after a reference period has passed from the first time point, and the reference period may be set differently depending on the measurement part of the first patient.

When the measurement part of the first patient is not detected as being in front of the camera of the first measuring device at step S1006, the process returns to step S1005 and the apparatus 400 maintain the waiting state for detecting the measurement part of the first patient.

When the measurement part of the first patient is detected as being in front of the camera of the first measuring device at step S1006, the apparatus 400 may generate a 1-2 image in which the blood flow state of the measurement part of the first patient is displayed at the second time point at step S1007.

Specifically, when the measurement part of the first patient is detected as being in front of the camera of the first measuring device at the second time point, the apparatus 400 emits laser light to the measurement part of the first patient through the camera of the first measuring device. When the emitted laser light is scattered from the surface of the measurement part of the first patient, the apparatus 400 may generate, using a laser speckle pattern, the 1-2 image in which the blood flow state of the measurement part of the first patient is displayed at the second time point.

At step S1008, the apparatus 400 may compare the 1-1 image and the 1-2 image to determine whether there is a change in the blood flow state of the measurement part of the first patient. In this case, the apparatus 400 may compare the blood flow state of the measurement part of the first patient at the first time point and the blood flow state of the measurement part of the first patient at the second time point based on the 1-1 image and the 1-2 image, and determine whether there is a change in the blood flow state of the measurement part of the first patient between the first time point and the second time point.

At step S1009, the apparatus 400 may check whether there is a change in the blood flow state of the measurement part of the first patient as a result of comparing the 1-1 image and the 1-2 image.

When it is determined that there is no change in the blood flow state of the measurement part of the first patient at step S1009, the process returns to step S1004 and the apparatus 400 may continue to display the 1-1 image on the screen of the monitor of the first measuring device.

When it is determined that there is a change in the blood flow state of the measurement part of the first patient at step S1009, the apparatus 400 may generate the second image in which the blood flow change of the measurement part of the first patient is displayed, based on the 1-1 image and the 1-2 image, at step S1010. In this case, the apparatus 400 may generate the second image in which the blood flow change is displayed by overlapping the 1-1 image and the 1-2 image and setting only the part in which a change in blood flow status is determined to exist to be highlighted.

That is, the blood flow state for the blood vessel measured at the first time point is displayed in the 1-1 image and the blood flow state for the blood vessel measured at the second time point is displayed in the 1-2 image. The apparatus 400 may compare the 1-1 image and the 1-2 image to detect the blood vessel having a change in the blood flow state, and may generate a second image in which the change in the blood flow state is displayed by displaying the detected blood vessel to be highlighted.

At step S1011, when the second image is generated, the apparatus 400 may display the second image on the screen of the monitor of the first measuring device.

After that, the apparatus 400 may acquire the second image as measurement information generated by measuring the blood flow state of the first patient.

Figure 11:
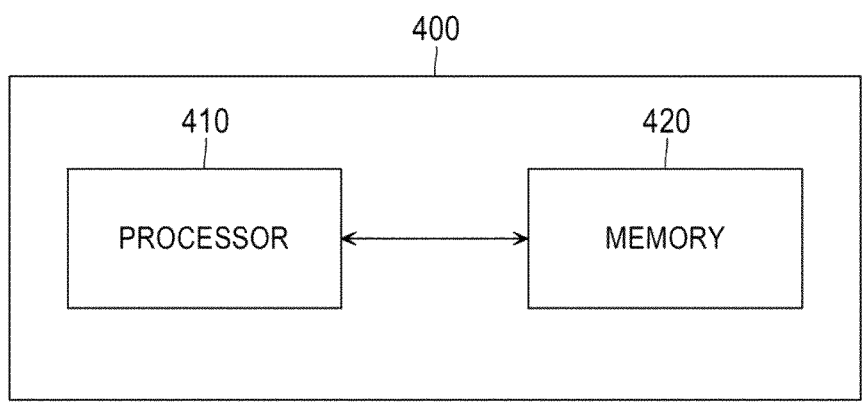
FIG. 11 is an exemplary diagram of a configuration of a device according to an embodiment.

FIG. 11 is an exemplary diagram of a configuration of an apparatus according to an embodiment.

An apparatus 400 according to an embodiment includes a processor 410 and a memory 420. The processor 410 may include at least one of the devices described above with reference to FIGS. 1 to 10, or may perform at least one method described above with reference to FIGS. 1 to 10. A person or organization using the apparatus 400 may provide a service related to some or all of the methods described above with reference to FIGS. 1 to 10.

The memory 420 may store information related to the methods described above or may store a program in which methods to be described below are implemented. The memory 420 may be a volatile memory or a non-volatile memory.

The processor 410 may execute a program and control the apparatus 400. Codes of the program executed by the processor 410 may be stored in the memory 420. The apparatus 400 may be connected to an external device (e.g. a personal computer or a network) through an input/output device (not shown) and exchange data through wired/wireless communication.

The embodiments described above may be implemented as hardware components, software components, and/or a combination of hardware components and software components. For example, the apparatuses, methods, and components described in embodiments may be implemented using one or more general-purpose computers or special-purpose computers, such as, for example, a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may perform an operating system (OS) and one or more software applications executed on the operating system. In addition, the processing device may access, store, manipulate, process, and generate data in response to the execution of software. For convenience of understanding, although one processing device has been described as being used, those skilled in the art may recognize that the processing device may include a plurality of processing elements and/or a plurality of types of processing elements. For example, the processing device may include a plurality of processors, or one processor and one controller. In addition, other processing configurations, such as parallel processors, are also possible.

The method according to the embodiment may be implemented in the form of program instructions that may be executed through various computer means and may be recorded in a computer-readable medium. The computer-readable media may also include the program instructions, data files, data structures, and the like alone or in combination. The program instructions recorded on the medium may be specially designed and configured for the embodiments, or may be known and available to those skilled in the computer software arts. Examples of the computer-readable recording medium include hardware devices such as magnetic media, such as a hard disk, a floppy disk, and a magnetic tape, optical media, such as CD-ROM and DVD, magneto-optical media such as a floptical disk, and a ROM, a RAM, and a flash memory. Examples of program instructions include machine code, such as those made by a compiler, as well as high-level language code that may be executed by a computer using an interpreter. The hardware devices described above may be configured to operate as one or more software modules to perform the operations of the embodiments, and vice versa.

Software may include computer program, code, instructions, or a combination of one or more of these, and may configure the processing device to operate as desired or may instruct the processing device independently or collectively. The software and/or data may be permanently or temporarily embodied in any type of machine, component, physical device, virtual equipment, computer storage media or device, or transmitted signal waves, in order to be interpreted by a processing device or to provide instructions or data to the processing device. The software may also be distributed over computer systems connected to a network, and stored or executed in a distributed manner. The software and data may be stored in one or more computer-readable recording media.

Although the embodiments have been described with limited drawings as described above, those skilled in the art may apply various technical modifications and variations thereto based on the matters described above. For example, even if the described techniques are performed in a different order than that in the described method, and/or components of the described systems, structures, devices, circuits, etc. are coupled or combined in a different form than those described, or are replaced or substituted by other components or equivalents, suitable results may be achieved.

Therefore, other implementations, other embodiments, and equivalents to the claims also fall within the scope of the claims described below.

The invention claimed is:

1. A system of providing a metaverse healthcare platform service for remote diagnosis and self-management, comprising:
   a device configured to perform the steps of:
       acquiring, when a health state of a patient is measured through a measuring device, measurement information generated by measuring the health status of the patient from the measuring device;

determining whether remote treatment is required for the patient on the basis of the measurement information;

when it is determined that the remote treatment for a treatment subject is required for the patient, outputting a message for guiding to wear an output device is output to a diagnostic booth;

when it is checked that the patient wears the output device, displaying a list of medical persons who are in charge of the treatment subject, is displayed on the output device;

if one of the medical persons is selected from the list through an operating device while the patient wears the operating device, displaying a screen of a virtual space, in which a treatment room of the one of the medical persons is implemented in a metaverse environment on the output device so as to allow the patient to be connected to the virtual space;

when movement within the virtual space is requested through the operating device, changing a point where the patient is located in the virtual space, and displaying the screen of the virtual space on the output device with the changed point as a center change; and when it is checked that the one of the medical persons is connected to the virtual space, displaying the measurement information on the virtual space so that the one of the medical persons performs the remote treatment on the patient in the virtual space, wherein the measuring device equipped in a diagnostic booth includes at least one of a blood pressure measuring device, a blood glucose measuring device, a blood flow measuring device, a heart rate measuring device, an electrocardiogram measuring device, or a body fat measuring device, wherein the metaverse environment includes an extended reality (XR), and the XR includes a virtual reality (VR), an augmented reality (AR), and a mixed reality (MR), wherein the diagnostic booth includes a chair, the measuring device, the output device, and the operating device, wherein the output device includes a head mounted display (HMD) configured to be mounted on a head of the patient and configured to output a VR/AR image to eyes of the patient, and wherein the operating device includes VR/AR gloves, each of the VR/AR gloves being configured to be worn on each hand of the patient to interact on the screen of the virtual space by tracking motions of each finger, each hand, and each wrist of the patient, implementing a motion image on at least one of the VR and the AR, expressing hardness of an object in the at least one of the VR and the AR through applying a tensile force of a magnitude of each finger, and expressing a touch through a vibration sensor in each of the VR/AR gloves.

2. The system of claim 1, wherein the displaying of the list on the output device comprises:
   checking, when treatment details of the patient is checked through medical information of the patient, whether there is a medical person who has treated the patient among the medical persons included in the list, based on the treatment details of the patient;
   selecting, when it is checked that there is only one medical person who has treated the patient in the list, the medical person who has treated the patient as a recommended medical person;

selecting, when it is checked that there are two or more medical persons who have treated the patient in the list, a medical person having the greatest number of treatments among the medical persons who have treated the patient as the recommended medical person;

checking, when it is checked that there is no medical person who has treated the patient in the list, whether there is a medical person who is in a treatment waiting state among the medical persons included in in the list;

selecting, when it is checked that there is only one medical person who is in the treatment waiting state in the list, the medical person who is in the treatment waiting state as the recommended medical person;

selecting, when it is checked that there are two or more medical persons who are in the treatment waiting state in the list, the medical person having the longest waiting time among the medical persons who are in the treatment waiting state as the recommended medical person;

selecting, when it is checked that there is no medical person who is in the treatment waiting state in the list, the medical person having the smallest number of reservations among the medical persons included in the list as the recommended medical person; and

when the recommended medical person is selected from the list, displaying a guide mark for recommending the recommended medical person on the output device, wherein the guide mark is displayed while being overlapped with the list.

3. The system of claim 1, wherein the determining of whether the remote treatment is required for the patient comprises the steps of:

checking a numerical value obtained by measuring the health state of the patient through the measuring device, based on the measurement information;

checking whether the numerical value is within a normal range;

determining, when it is checked that the numerical value is within the normal range, that the remote treatment is not required for the patient;

checking, when it is checked that the numerical value is out of the normal range, whether the numerical value is within a warning range;

determining, when it is checked that the numerical value is out of the warning range, that re-measurement of the health state of the patient is required; and determining, when it is checked that the numerical value is out of the warning range, that the remote treatment is required for the patient.

* * * * *